(12) United States Patent
Kobayashi et al.

(10) Patent No.: US 11,219,422 B2
(45) Date of Patent: Jan. 11, 2022

(54) IMAGE DISPLAYING SYSTEM, IMAGE PROCESSING APPARATUS AND X-RAY IMAGING SYSTEM

(71) Applicant: CANON MEDICAL SYSTEMS CORPORATION, Otawara (JP)

(72) Inventors: Yoshimasa Kobayashi, Nasushiobara (JP); Hisato Takemoto, Nasushiobara (JP); Toru Takahashi, Nasushiobara (JP); Tomio Maehama, Nasushiobara (JP); Hideaki Tanaka, Otawara (JP); Naoya Fujita, Otawara (JP); Manabu Tanaka, Otawara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 0 days.

(21) Appl. No.: 15/917,870

(22) Filed: Mar. 12, 2018

(65) Prior Publication Data
US 2018/0263582 A1    Sep. 20, 2018

(30) Foreign Application Priority Data

Mar. 14, 2017  (JP) .............................. JP2017-048351
Mar. 1, 2018   (JP) .............................. JP2018-036239

(51) Int. Cl.
*A61B 6/00*    (2006.01)
*A61B 90/00*   (2016.01)
(Continued)

(52) U.S. Cl.
CPC ............ *A61B 6/462* (2013.01); *A61B 6/4441* (2013.01); *A61B 90/361* (2016.02);
(Continued)

(58) Field of Classification Search
CPC .......... A61B 6/04; A61B 6/4447; A61B 6/027
See application file for complete search history.

(56) References Cited

U.S. PATENT DOCUMENTS

2004/0013239 A1* 1/2004 Gregerson .............. A61B 6/02
                                                 378/197
2009/0034820 A1* 2/2009 Sugiyama ............ A61B 6/4441
                                                 382/132

(Continued)

FOREIGN PATENT DOCUMENTS

CN    104298344 A    1/2015
JP    2005-335410    12/2005

OTHER PUBLICATIONS

Combined Chinese Office Action and Search Report dated Feb. 2, 2021 in corresponding Chinese Patent Application No. 20180208034.8 (with English Translation of Category of Cited Documents), 36 pages.

*Primary Examiner* — David P Porta
*Assistant Examiner* — Mamadou Faye
(74) *Attorney, Agent, or Firm* — Oblon, McClelland, Maier & Neustadt, L.L.P.

(57) ABSTRACT

An image displaying system according to an embodiment includes an observation target device, a display device and processing circuitry. The display device is configured to display an image. The processing circuitry is configured to: arrange a three-dimensional model relating to the observation target device in a virtual space; acquire data indicating a relative positional relationship between an operator and the observation target device; generate an image of a three-dimensional model included in a blind area when viewed from the operator, based on the data indicating the relative positional relationship and on the three-dimensional model arranged in the virtual space; and display the image on the display device.

18 Claims, 12 Drawing Sheets

(51) Int. Cl.
*G01N 23/046* (2018.01)
*A61B 90/50* (2016.01)
*A61B 6/03* (2006.01)

(52) U.S. Cl.
CPC ............ *G01N 23/046* (2013.01); *A61B 6/032* (2013.01); *A61B 6/463* (2013.01); *A61B 6/464* (2013.01); *A61B 6/547* (2013.01); *A61B 2090/367* (2016.02); *A61B 2090/372* (2016.02); *A61B 2090/373* (2016.02); *A61B 2090/376* (2016.02); *A61B 2090/502* (2016.02); *G01N 2223/40* (2013.01); *G06T 2207/10116* (2013.01)

(56) References Cited

U.S. PATENT DOCUMENTS

| | | | | |
|---|---|---|---|---|
| 2014/0049629 | A1* | 2/2014 | Siewerdsen | A61B 34/20 348/77 |
| 2015/0363979 | A1* | 12/2015 | Takano | A61B 6/461 345/633 |
| 2017/0368369 | A1* | 12/2017 | Heinrich | G06T 7/251 |
| 2018/0271511 | A1* | 9/2018 | Stanton | A61B 17/0218 |
| 2019/0164354 | A1* | 5/2019 | Sasaki | G06T 19/00 |
| 2019/0328481 | A1* | 10/2019 | Kamikawa | A61B 90/20 |

* cited by examiner

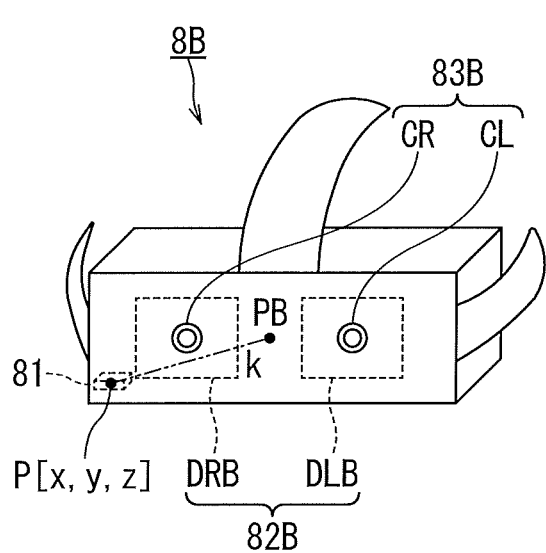
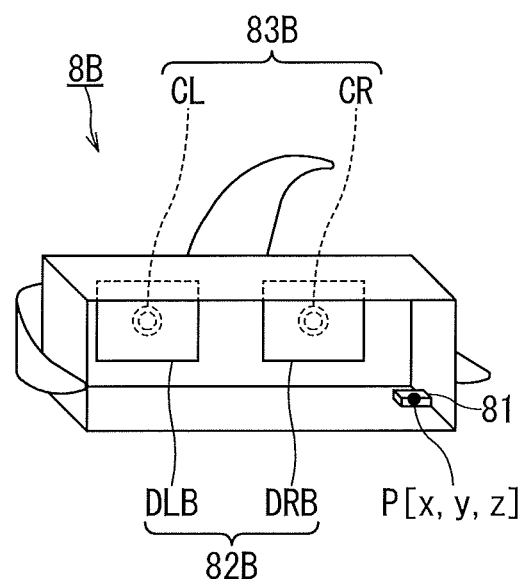
FIG. 7A  FIG. 7B
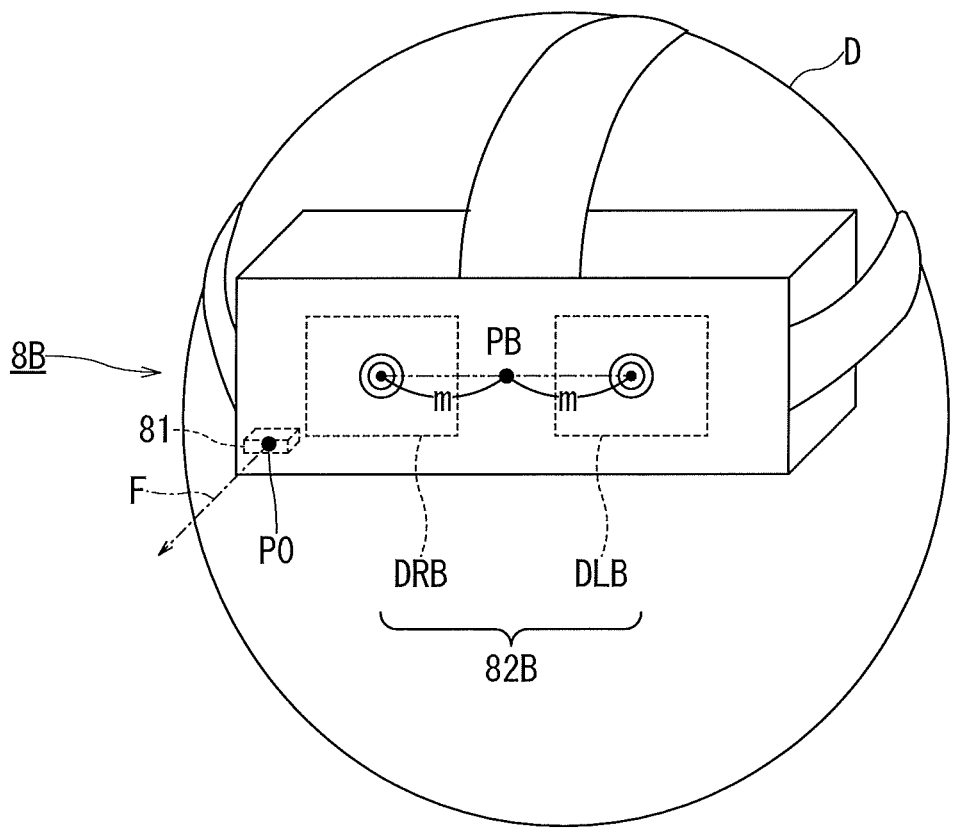
FIG. 7C

IMAGE DISPLAYING SYSTEM, IMAGE PROCESSING APPARATUS AND X-RAY IMAGING SYSTEM

CROSS-REFERENCE TO RELATED APPLICATION

This application is based upon and claims the benefit of priority from Japanese Patent Application No. 2017-048351, filed on Mar. 14, 2017, and Japanese Patent Application No. 2018-036239, filed on Mar. 1, 2018, the entire contents of each of which are incorporated herein by reference.

FIELD

An embodiment as an aspect of the present invention relates to an image displaying system, an image processing apparatus and an X-ray imaging system.

BACKGROUND

The X-ray Angio system includes a movable device, such as a C-arm, an X-ray emitting device, and an X-ray detecting device, which can move in a relatively flexible range of motion. When performing arc movement of the C-arm by an operation of an operator, the operator needs to care about a collision of the moving X-ray emitting device (or X-ray detecting device) with a bed device, observing a position of the X-ray emitting device at a tip of the C-arm and a position of the bed device. In particular, in order to avoid the collision at a blind spot caused by a subject and the bed device as seen from the operator, the operator must perform C-arm movement, paying greater attention than usual, or looking into a place which is the blind spot, with a different viewpoint.

An X-ray Angio system according to the prior art includes a touch sensor. This X-ray Angio system performs, when the touch sensor recognizes that the X-ray emitting device (or the X-ray detecting device) was collided with the bed device by the arc movement of the C-arm, control to slightly evacuate the C-arm in a direction opposite to a direction of the arc movement.

There is also an X-ray Angio system equipped with a capacitive sensor or an infrared sensor. This X-ray Angio system performs, when the touch sensor recognizes that the X-ray emitting device (or the X-ray detecting device) is likely to collide with the bed device by the arc movement of the C-arm, so as not to cause the C-arm to move further arc. Thereby, it is possible to avoid the collision of the X-ray emitting device with the bed device.

In the other technical fields, there is also a technique of optically imaging the blind spot caused when viewed from the operator in a certain place, acquiring an optical image, and displaying the optical image.

BRIEF DESCRIPTION OF THE DRAWINGS

In accompanying drawings.

Figure 2A:
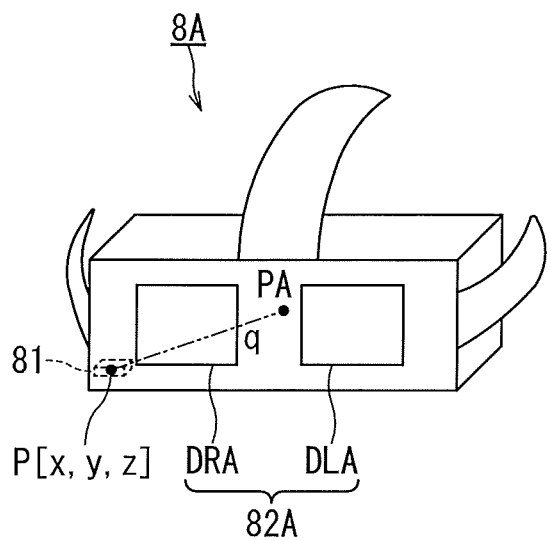
Figure 2B:
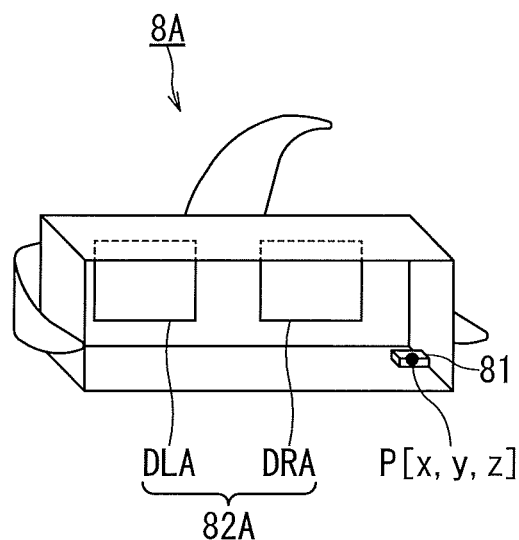
Figure 2C:
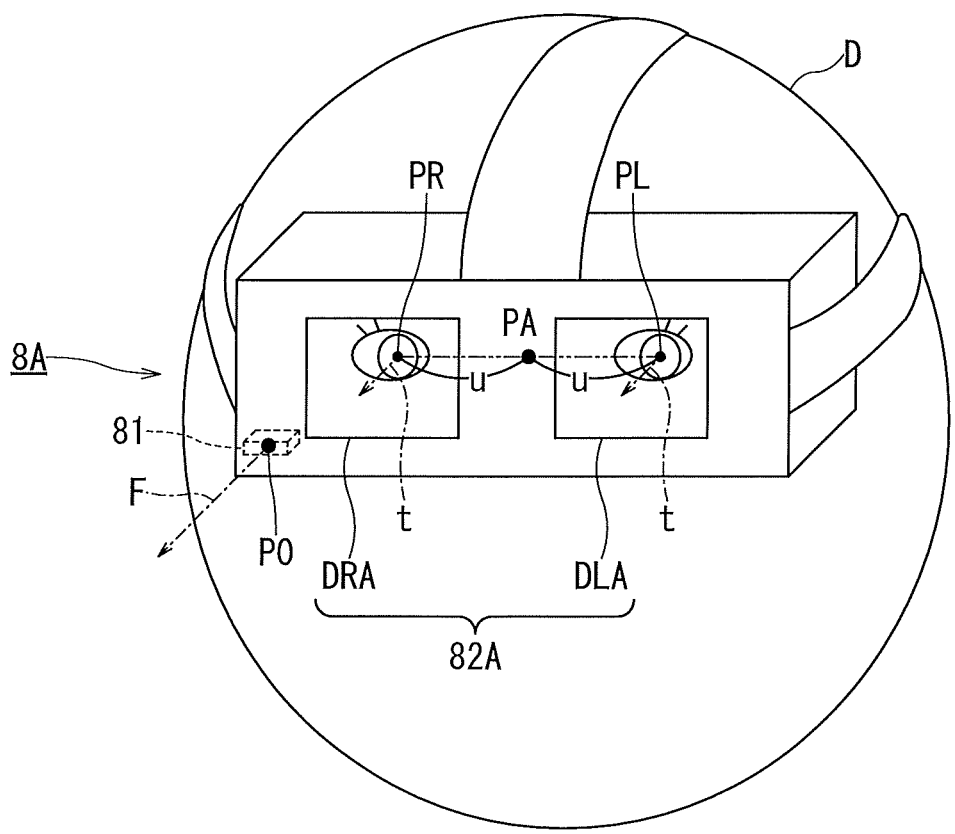
Figure 3:
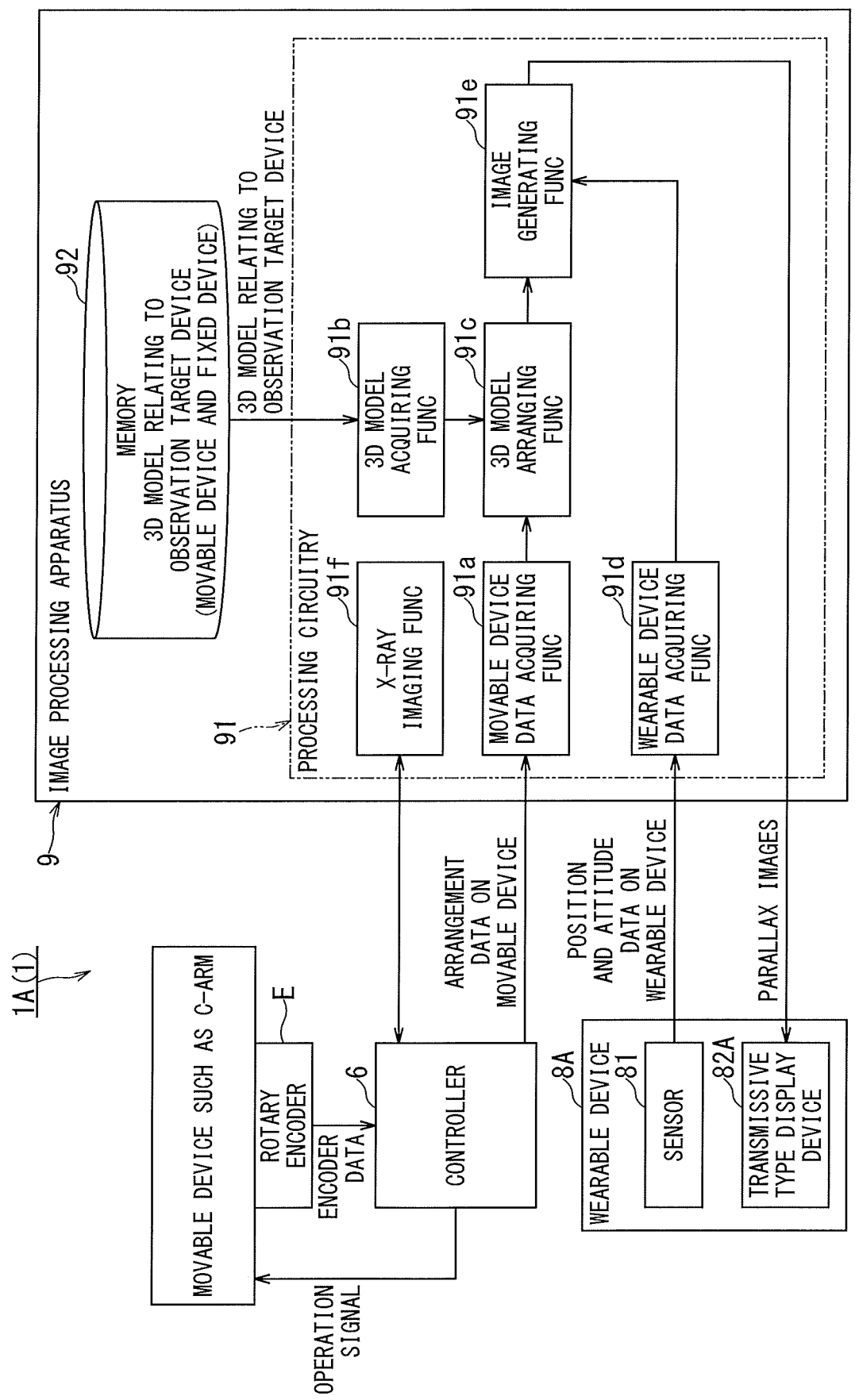
Figure 4:
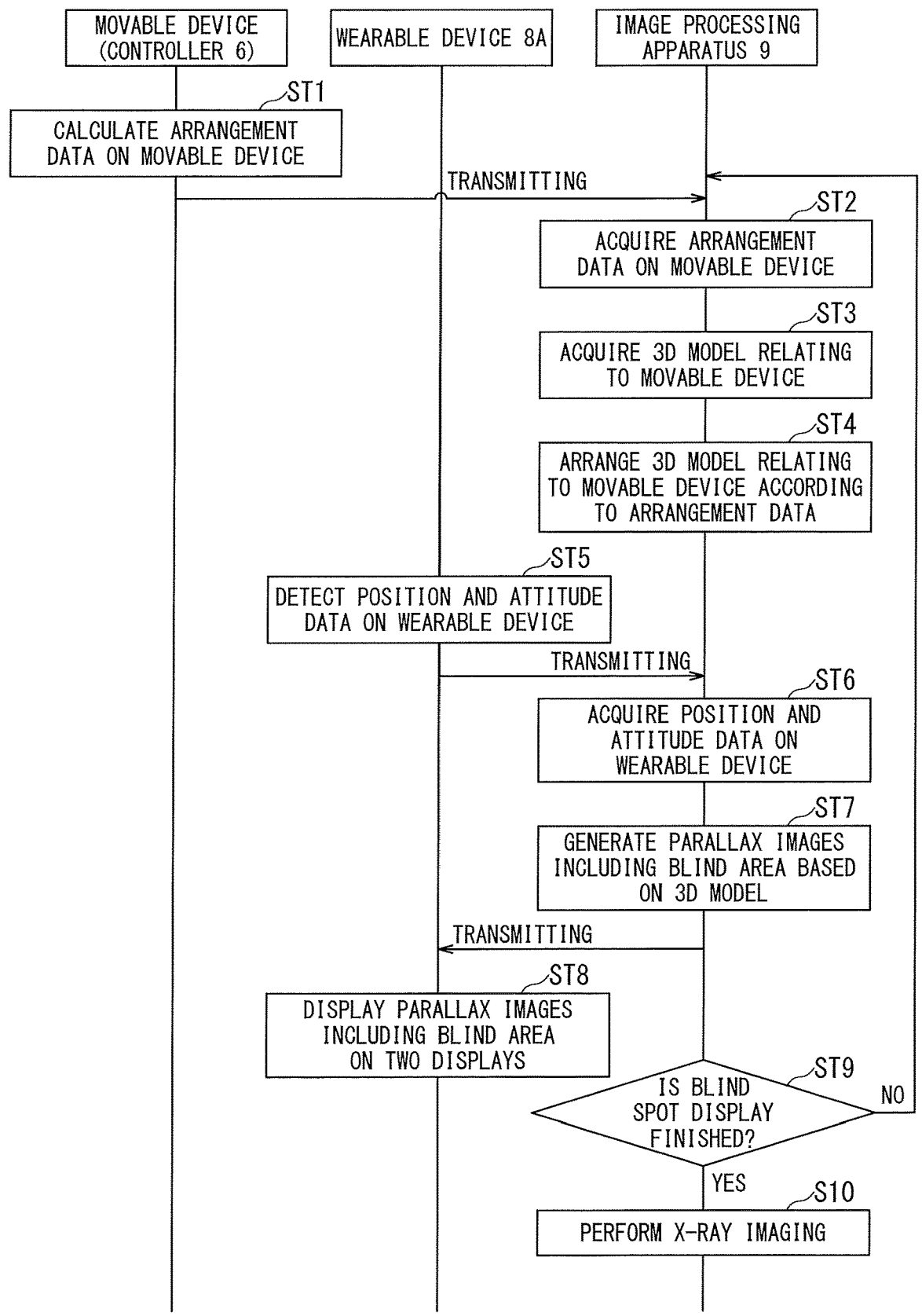
Figure 5A:
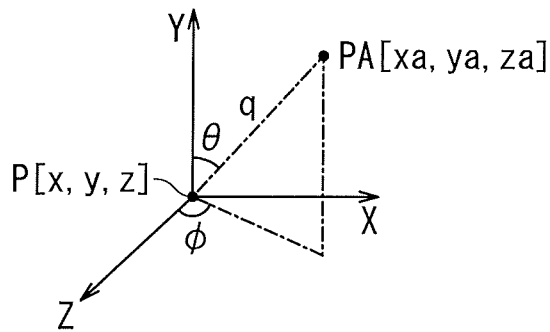
Figure 5C:
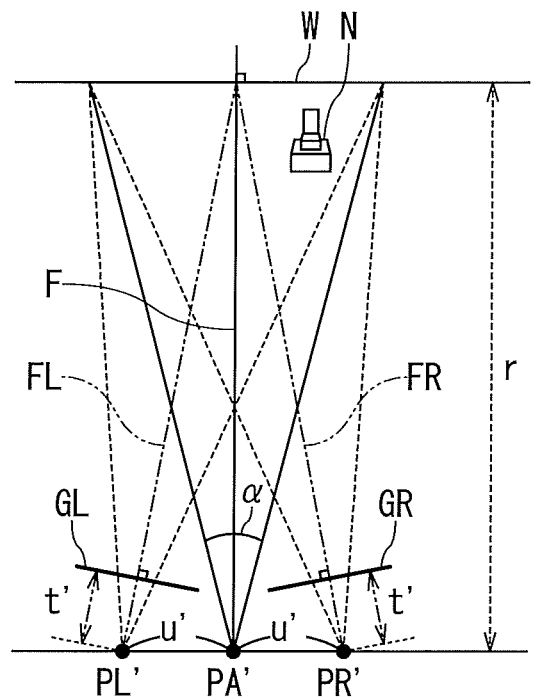
Figure 5B:
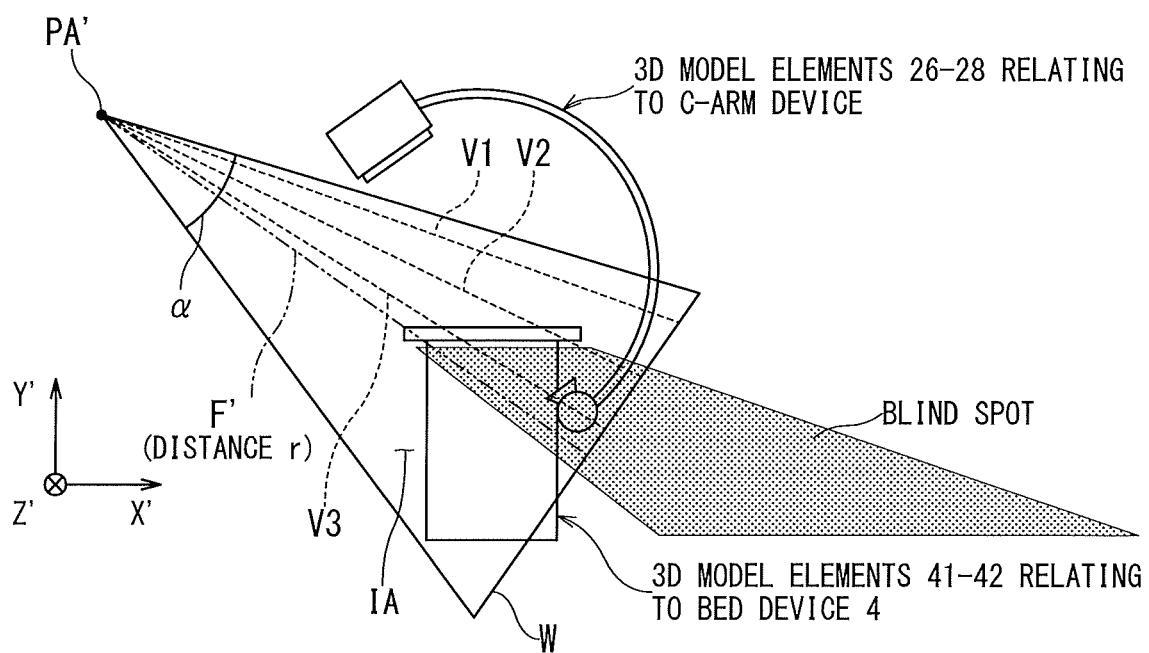
Figure 6A:
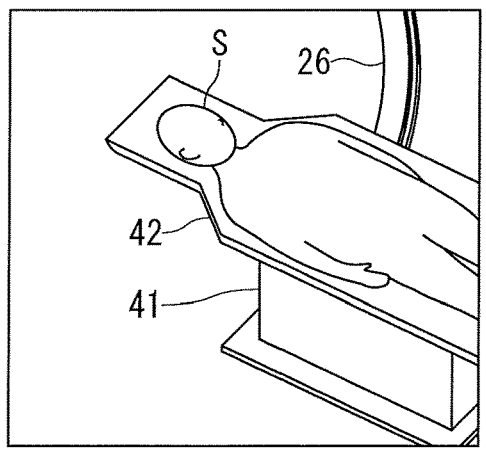
Figure 6B:
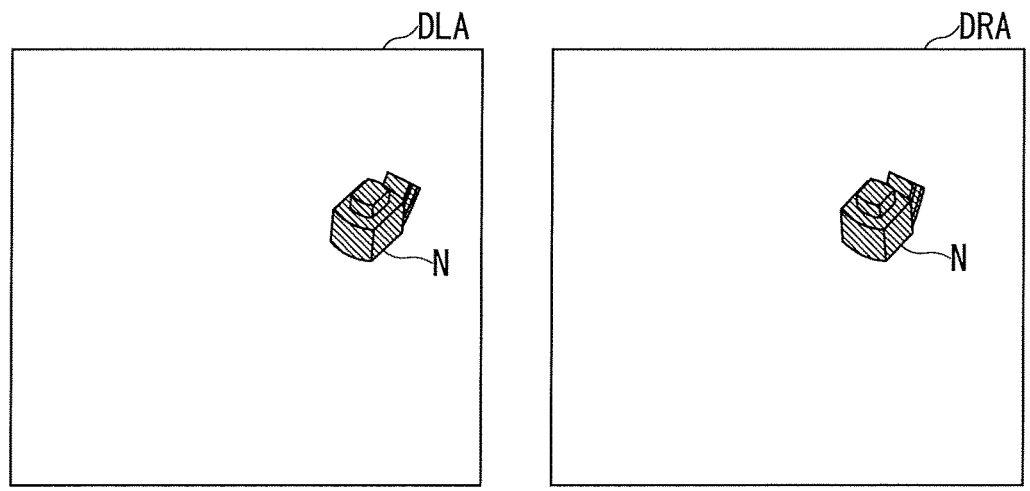
Figure 6C:
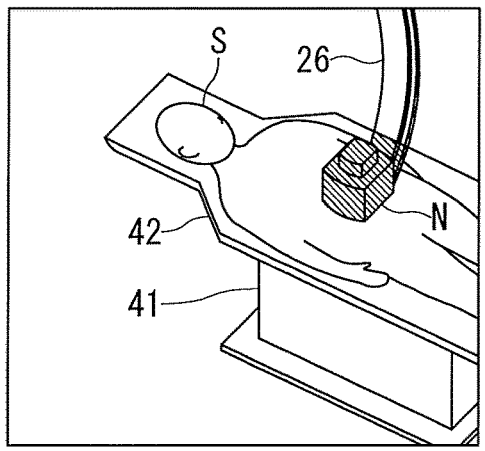
Figure 8:
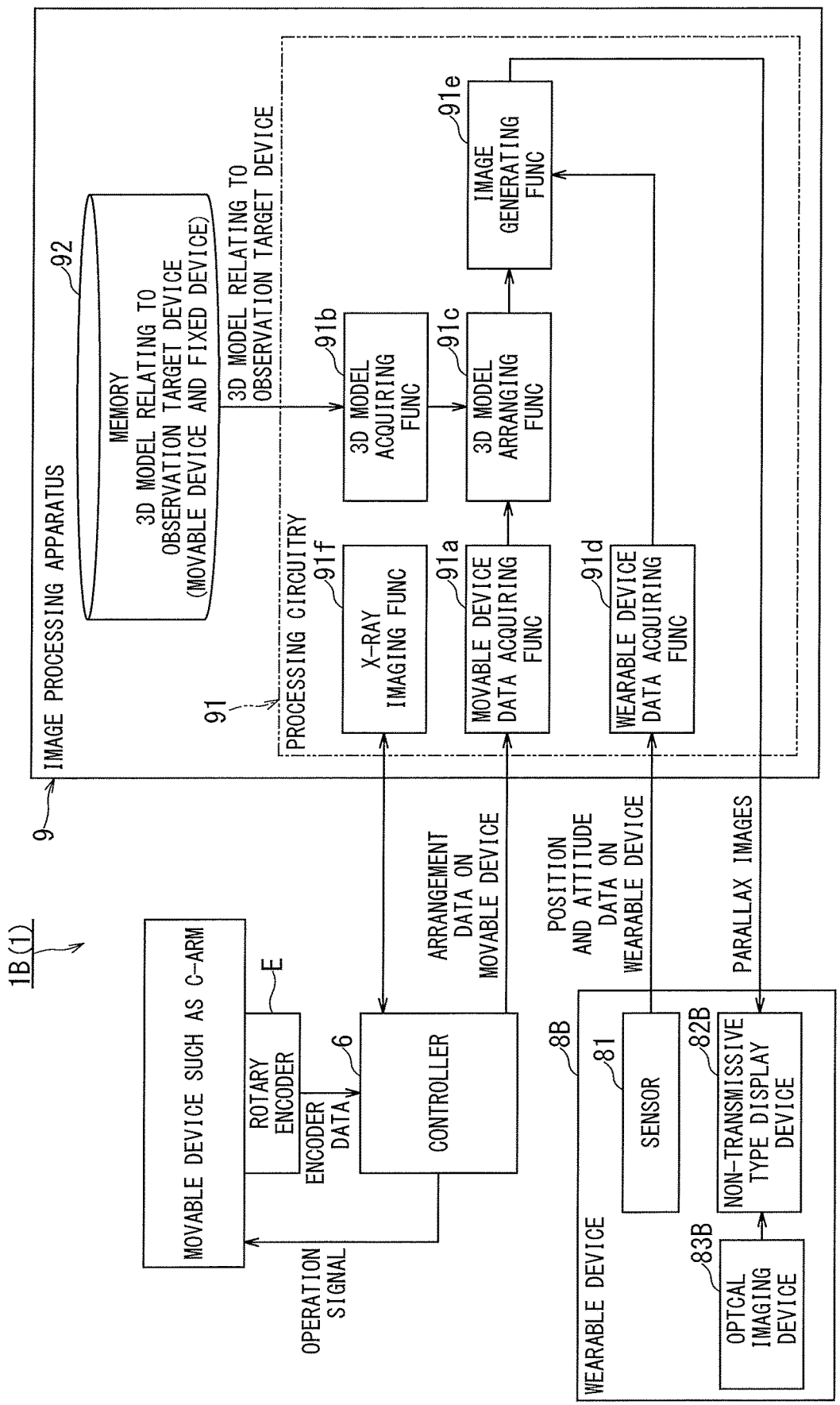
Figure 9:
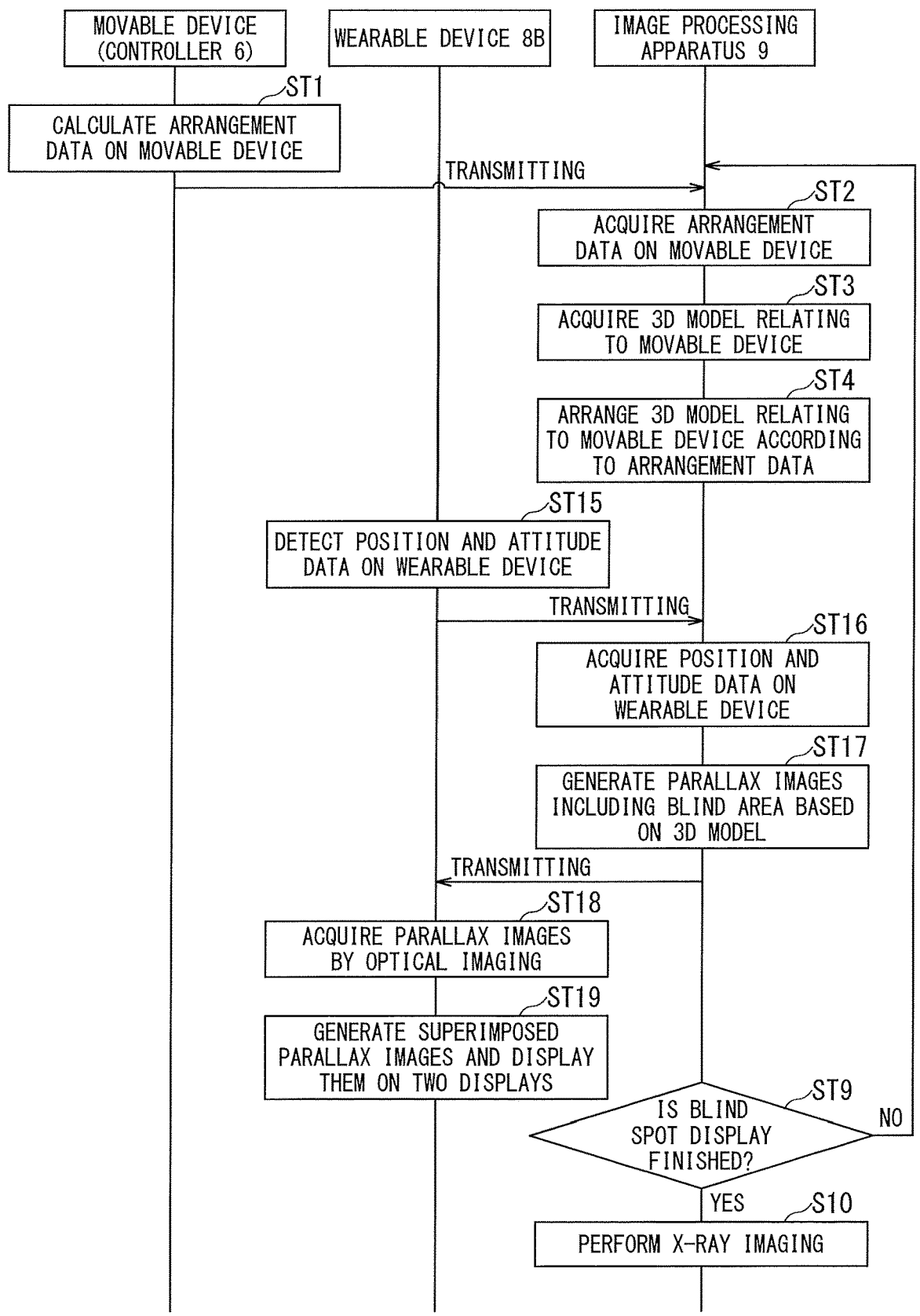
Figure 10A:
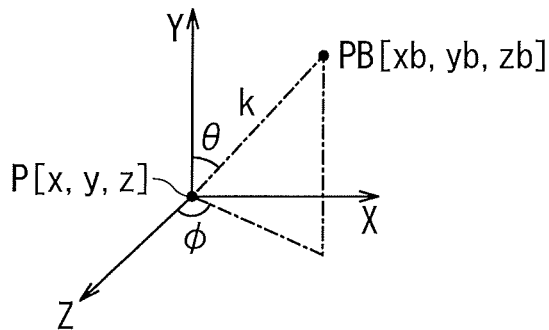
Figure 10C:
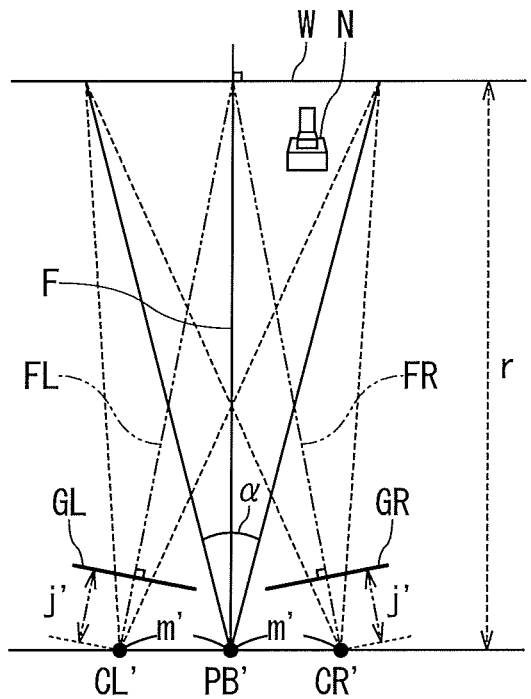
Figure 10B:
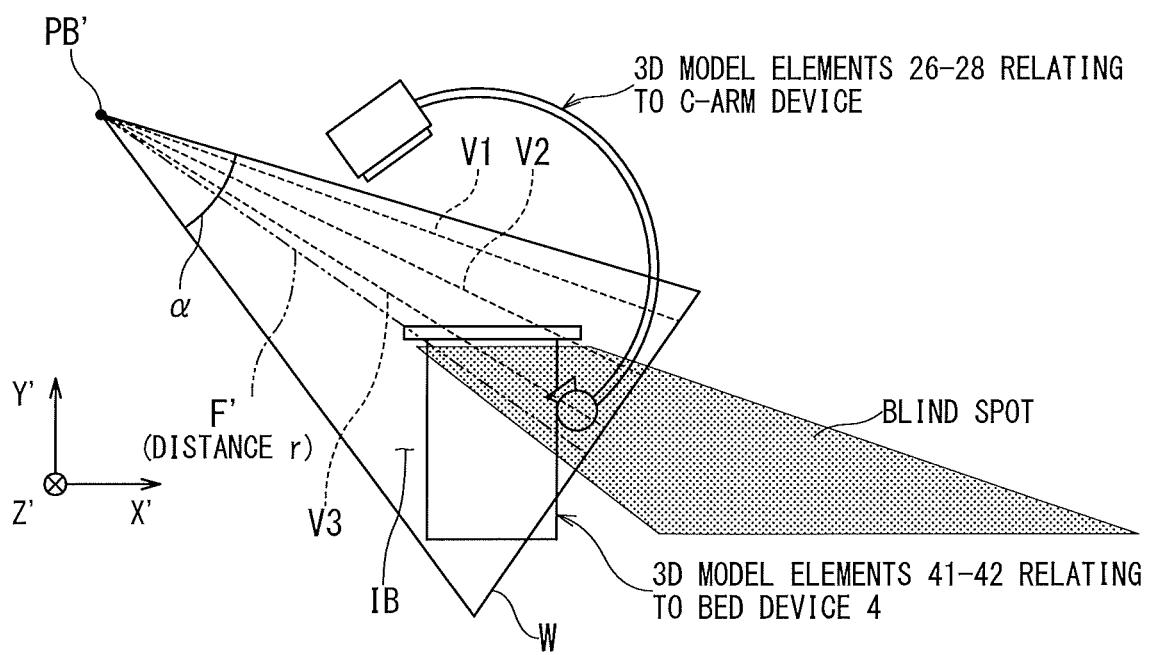
Figure 11:
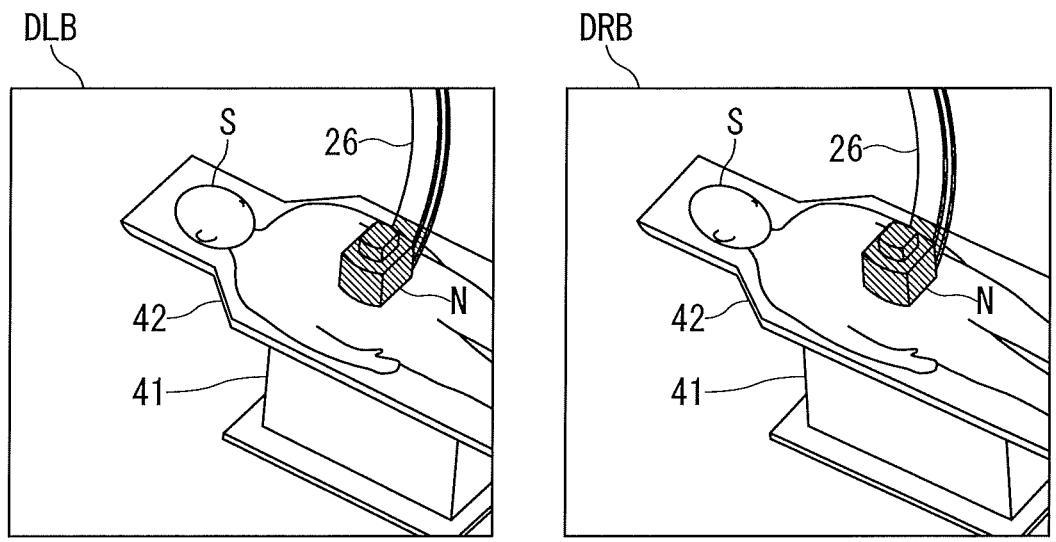
Figure 12:
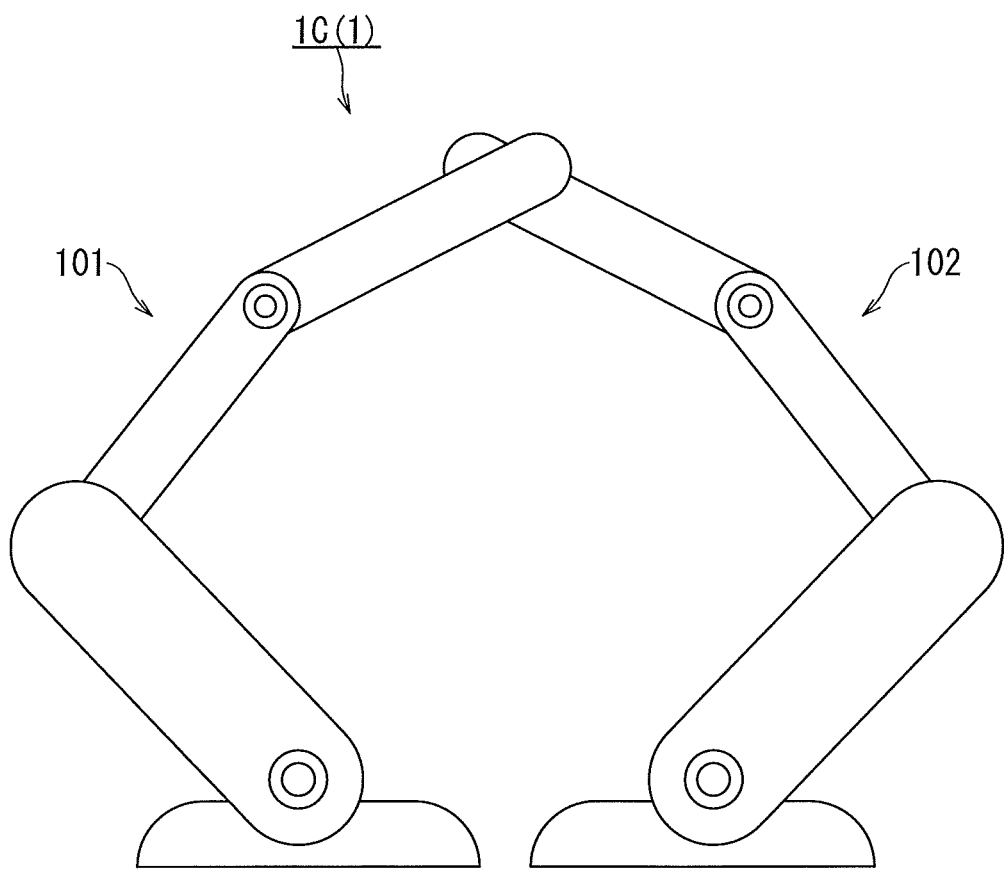
Figure 13:
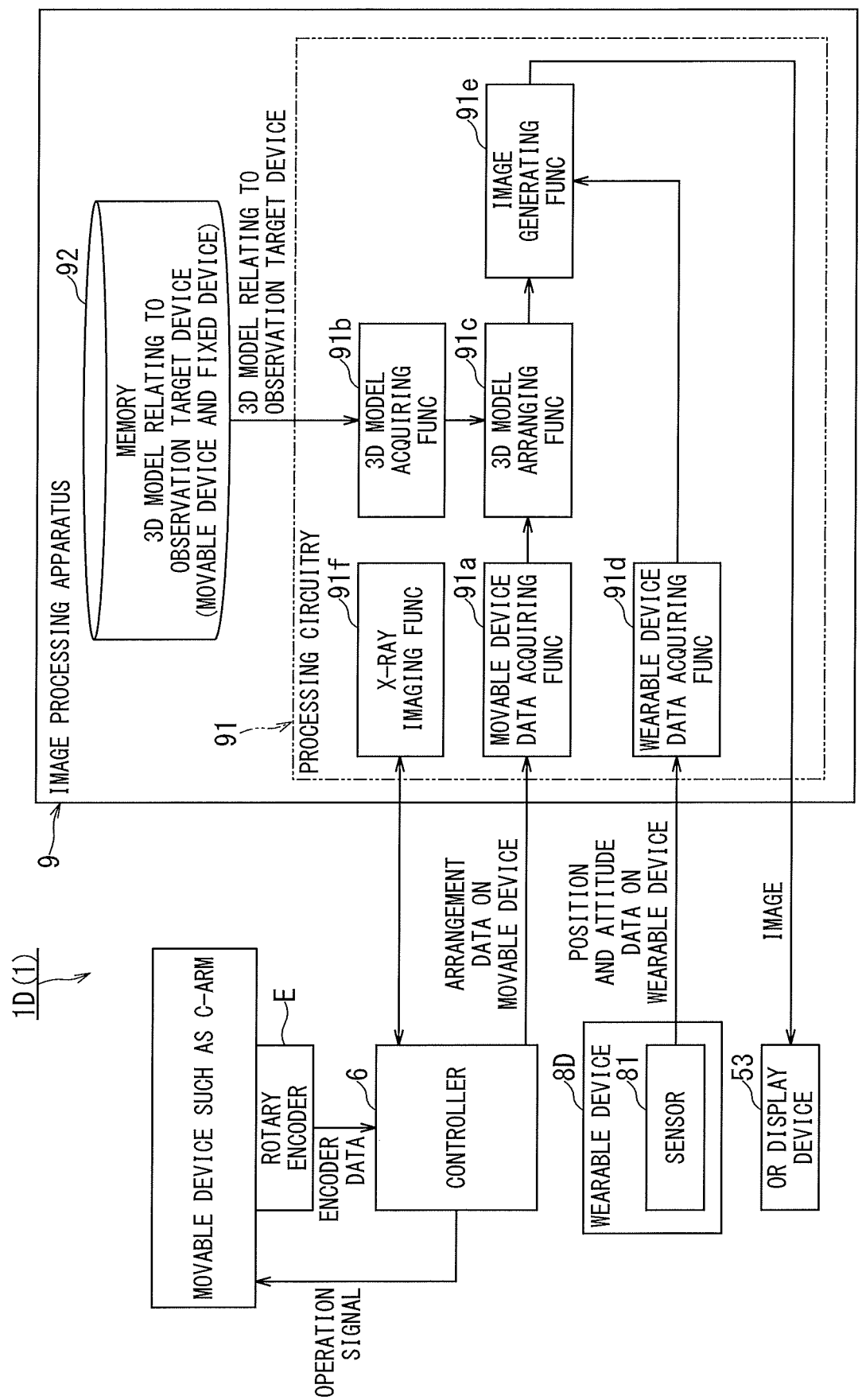

Each of FIGS. 2A and 2B is a diagram showing a configuration example of a wearable device arranged in the X-ray imaging system according to the first embodiment;

FIG. 2C is a diagram showing a worn state of the wearable device, in the X-ray imaging system according to the first embodiment;

FIG. 3 is a block diagram showing functions of the X-ray imaging system according to the first embodiment;

FIG. 4 is a flowchart showing an example of an operation of the X-ray imaging system according to the first embodiment;

FIG. 5A is a diagram for explaining a method of setting position data of the wearable device in the X-ray imaging system according to the first embodiment;

FIG. 5B is a diagram for explaining a method of specifying a blind area in the X-ray imaging system according to the first embodiment;

FIG. 5C is a diagram for explaining a method of generating parallax images including the blind area in the X-ray imaging system according to the first embodiment;

FIG. 6A is a schematic diagram showing a field of view of an operator in the prior art;

FIG. 6B is a diagram showing parallax images displayed on the transmissive type displays of the wearable device, in the X-ray imaging system according to the first embodiment;

FIG. 6C is a schematic diagram showing a field of view of the operator wearing the wearable device in the X-ray imaging system according to the first embodiment;

Each of FIGS. 7A and 7B is a diagram showing a configuration example of a wearable device arranged in the X-ray imaging system according to a second embodiment;

FIG. 7C is a diagram showing a worn state of the wearable device, in the X-ray imaging system according to the second embodiment;

FIG. 8 is a block diagram showing functions of the X-ray imaging system according to the second embodiment;

FIG. 9 is a flowchart showing an example of an operation of the X-ray imaging system according to the second embodiment;

FIG. 10A is a diagram for explaining a method of setting position data of the wearable device in the X-ray imaging system according to the second embodiment;

FIG. 10B is a diagram for explaining a method of specifying a blind area in the X-ray imaging system according to the second embodiment;

FIG. 10C is a diagram for explaining a method of generating parallax images including the blind area in the X-ray imaging system according to the second embodiment;

FIG. 11 is a diagram showing parallax images displayed on the non-transmissive type displays of the wearable device, in the X-ray imaging system according to the second embodiment;

FIG. 12 is a schematic diagram showing the overall configuration of a robot arm system according to a third embodiment; and FIG. 13 is a block diagram showing functions of the X-ray imaging system according to a fourth embodiment.

DETAILED DESCRIPTION

An image displaying system, an image processing apparatus and an X-ray imaging system according to embodiments will be described in detail with reference to the drawings.

The image displaying system according to an embodiment includes an observation target device, a display device and processing circuitry. The display device is configured to display an image. The processing circuitry is configured to: arrange a three-dimensional model relating to the observation target device in a virtual space; acquire data indicating a relative positional relationship between an operator and the observation target device; generate an image of a three-dimensional model included in a blind area when viewed from the operator, based on the data indicating the relative positional relationship and on the three-dimensional model arranged in the virtual space; and display the image on the display device.

The image displaying system 1 according to the present invention is a system in which an operator operates, while observing an observation target device including at least one independently movable device, the movable device moving according to his/her own operation. The image displaying system 1 may include at least two movable devices and may not include a fixed device, or may include at least one movable device and a fixed device. The image displaying system 1 is a concept including an X-ray imaging system including an X-ray tube, an X-ray detecting device, and the like. First, an X-ray imaging system 1A (shown in FIGS. 1 to 6) will be described as a first embodiment of the image displaying system 1. Second, an X-ray imaging system 1B (shown in FIGS. 7 to 11) will be described as a second embodiment of the image displaying system 1. Third, a robot arm system 1C (shown in FIG. 12) will be described as a third embodiment of the image displaying system 1. Fourth, an X-ray imaging system 1D (shown in FIG. 13) will be described as a fourth embodiment of the image displaying system 1.

1. First Embodiment of Image Displaying System 1

Figure 1:
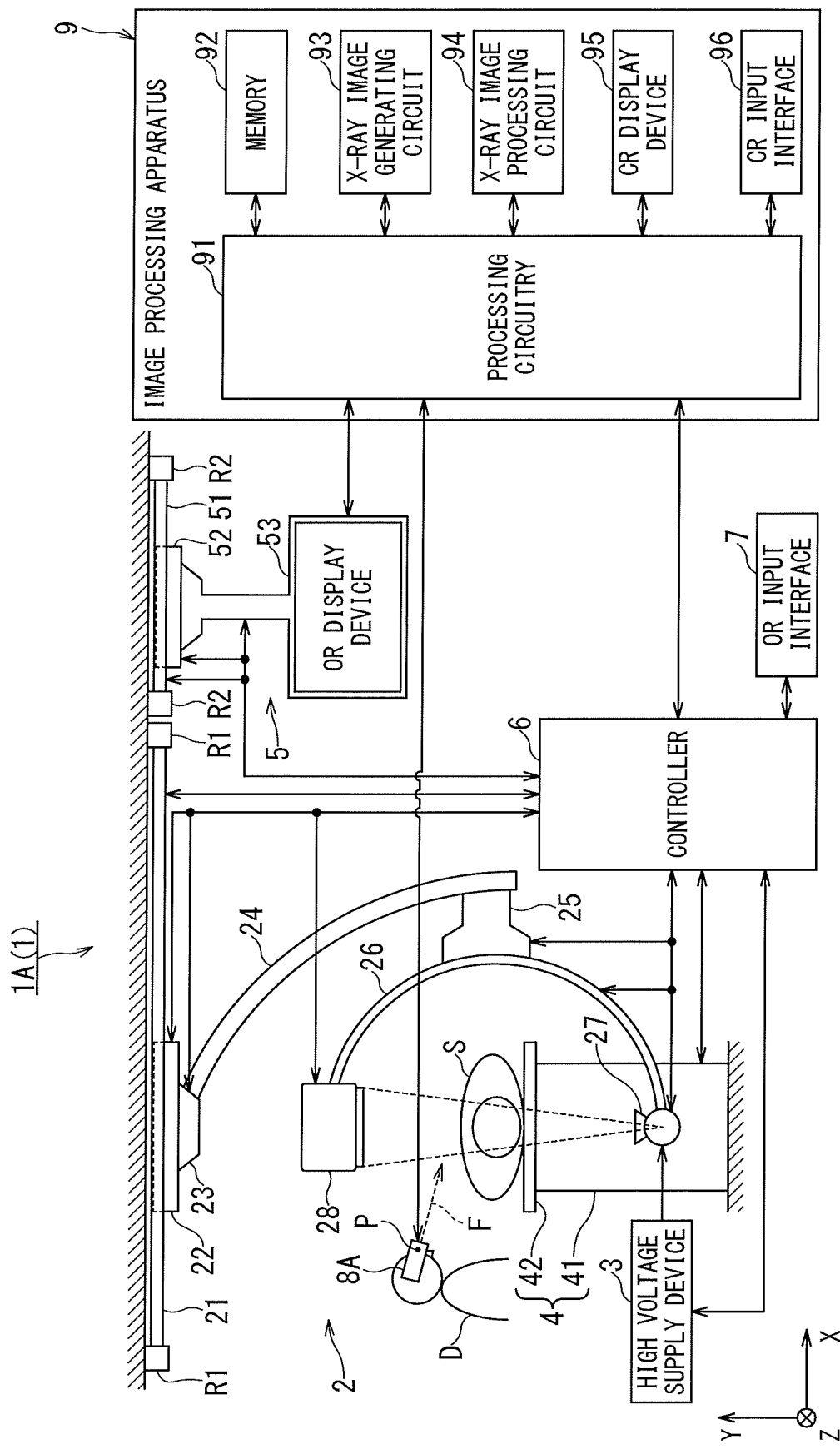
FIG. 1 is a schematic diagram showing the overall configuration of an X-ray imaging system according to a first embodiment.

FIG. 1 is a schematic diagram showing the overall configuration of an X-ray imaging system according to a first embodiment.

FIG. 1 shows an X-ray imaging system 1A according to a first embodiment, for example, an X-ray Angio system. FIG. 1 shows a case where the X-ray imaging system 1A includes a C-arm which is an overhead traveling type and under-tube type, but the present invention is not limited to this case. The X-ray imaging system 1A may be provided with an overhead traveling Ω-arm and a floor-standing type C-arm, may be provided with only an overhead traveling Ω-arm, or may be provided with only a floor-mounted C-arm. Alternatively, the X-ray imaging system 1A may be provided with an over-tube type C-arm or Ω-arm.

The X-ray imaging system 1A generically includes a first holding device 2, a high voltage supply device 3, a bed device 4, a second holding device 5, a controller 6, an operation room input circuit 7, a wearable device 8A and an image processing apparatus (workstation) 9. The first holding device 2, the high voltage supply device 3, the bed device 4, the second holding device 5, the controller 6, and the operation room input circuit 7 are generically installed in a surgical operation room (examination/treatment room). The wearable device 8A is used in the surgical operation room. The image processing apparatus 9 is installed in a control room adjacent to the surgical operation room.

The first holding device 2 includes an X-axis direction rail 21, a carriage 22, a vertical axis rotating device 23, a suspension arm 24, a C-arm rotating device 25, a C-arm 26, an X-ray emitting device 27 and an X-ray detecting device 28.

The X-axis direction rail 21 extends in an X-axis direction (short axis direction of the table 42) and is supported by the Z-axis direction rail R1 via rollers (not shown) at both ends thereof. The Z-axis direction rail R1 extends in a Z-axis direction (long axis of the table 42) and is supported by a ceiling. The X-axis direction rail 21 is able to move, under control of the controller 6 or a manual operation, in the Z-axis direction along the Z-axis direction rail R1. That is, the X-axis direction rail 21 is able to perform a slide in the Z-axis direction.

The carriage 22 is supported on the X-axis direction rail 21 via rollers (not shown). The carriage 22 is able to move, under control of the controller 6 or a manual operation, in the X-axis direction along the X-axis direction rail 21. That is, the carriage 22 is able to perform a slide in the X-axis direction.

The X-axis direction rail 21 supporting the carriage 22 is able to slide along the Z-axis direction rail R1 in the Z-axis direction. The carriage 22 is able to slide along the X-axis direction rail 21 in the X-axis direction. Therefore, the carriage 22 is able to slide in the surgical operation room in the horizontal direction (X-axis direction and Z-axis direction).

The vertical axis rotating device 23 is rotatably supported by the carriage 22 via rollers (not shown). The vertical axis rotating device 23 is able to move, under control of the controller 6 or a manual operation, in the vertical axis rotating direction. That is, the vertical axis rotating device 23 is able to rotate in the vertical axis rotating direction.

The suspension arm 24 is supported by the vertical axis rotating device 23, and is able to move integrally with the vertical axis rotating device 23.

The C-arm rotating device 25 is supported by the suspension arm 24 via rollers (not shown). The C-arm rotating device 25 is able to move, under control of the controller 6 or a manual operation, in the horizontal axis rotating direction. That is, the C-arm rotating device 25 is able to rotate along the horizontal axis rotating direction.

The C-arm 26 is supported by the C-arm rotating device 25. The X-ray emitting device 27 and the X-ray detecting device 28 are opposed to each other with a subject S as the center. The C-arm 26 is supported by the C-arm rotating device 25 via rollers (not shown) engaged with curved rails (not shown) of the C-arm rotating device 25. The C-arm 26 is able to move, under control of the controller 6 or a manual operation, in a curvature direction along the curved rail. That is, the C-arm 26 is able to arc move along the curvature direction.

The X-ray emitting device 27 is provided at one end of the C-arm 26 via rollers (not shown). The X-ray emitting device 27 is able to move, under control of the controller 6 or a manual operation, along a direction (SID direction: Source Image Distance) connecting the center of an X-ray tube (not shown) and the center of an X-ray detector (not shown). That is, the X-ray emitting device 27 is able to forward and backward move along the SID direction.

The X-ray emitting device 27 is provided with an X-ray tube (X-ray source) (not shown) and a movable diaphragm device (not shown). The X-ray tube receives high-voltage power from the high-voltage supply device 3 and generates X-rays according to conditions of high voltage power. The movable diaphragm device movably supports, under the control of the controller 6, diaphragm blades made of a material which shields the X-rays at an X-ray emitting aperture of the X-ray tube. Note that a linear quality adjustment filter (not shown) for adjusting the quality of the X-rays generated by the X-ray tube may be provided on the front face of the X-ray tube.

The X-ray detecting device 28 is provided on the other end of the C-arm 26 via rollers (not shown) so as to face the X-ray emitting device 27. The X-ray detecting device 28 is able to move, under control of the controller 6 or a manual operation, along the SID direction. That is, the X-ray detecting device 28 is able to forward and backward move along the SID direction. The X-ray detecting device 28 is able to move, under control of the controller 6 or a manual operation, along a rotating direction around the SID direction. That is, the X-ray detecting device 28 is able to rotate along the rotating direction around the SID direction.

The X-ray detecting device 28 includes an FPD (Flat Panel Detector) and an A/D (Analog to Digital) conversion circuit (not shown). The FPD has multiple detecting elements arranged two-dimensionally. Between each detecting element of the FPD, the scanning line and the signal line are disposed so as to be orthogonal to each other. A grid (not shown) may be provided on the front face of the FPD. In order to absorb scattered rays incident on the FPD and to improve the contrast of an X-ray image, the grid is formed by alternately arranging a grid plate, made from lead having a large X-ray absorption, and aluminum, wood and the like which are easy to transmit. The A/D conversion circuit converts projection data of a time-series analog signal (video signal) output from the FPD into a digital signal, and outputs it to the image processing apparatus 9.

Note that the X-ray detecting device 28 is an I.I. (Image Intensifier)-TV system. The I.I.-TV system converts X-rays transmitted through the subject S and directly incident X-rays into visible light, obtains highly sensitive projection data by doubling the brightness in a process of light-electron-light conversion, and converts the optical projection data into an electric signal using a CCD (Charge Coupled Device) imaging element.

The high voltage supply device 3 is able to supply high voltage power to the X-ray tube of the X-ray emitting device 27 under the control of the controller 6.

The bed device 4 includes a bed main body 41 and a table 42. The lower part of the bed device 4 is supported on a floor. The upper part of the bed main body 41 is able to move, under the control of the controller 6, in the Y-axis direction with respect to the lower part. That is, the upper part of the bed main body 41 is able to slide, along the Y-axis direction, with respect to the lower part.

The table 42 is supported by the bed main body 41 via rollers (not shown). The table 42 is capable of placing the subject S thereon. The table 42 is able to move along the Y-axis direction by the movement of the upper part of the bed main body 41 along the Y-axis direction. That is, the table 42 is able to slide along the Y-axis direction. The table 42 is able to move, under control of the controller 6, along the X-axis direction or the Z-axis direction. That is, the table 42 is able to slide along the X-axis direction or the Z-axis direction. In addition, the table 42 is able to perform a rolling and a tilting under control of the controller 6.

The second holding device 5 includes an X-axis direction rail 51, a carriage 52, and an operation room display device 53.

The X-axis direction rail 51 extends in the X-axis direction (short axis of the table 42) and is supported by the Z-axis direction rail R2 via rollers (not shown) at both ends thereof. The Z-axis direction rail R2 extends in the Z-axis direction (long axis of the table 42) and is supported by the ceiling. The X-axis direction rail 51 is able to move, under control of the controller 6 or a manual operation, in the Z-axis direction along the Z-axis direction rail R2. That is, the X-axis direction rail 51 is able to slide in the Z-axis direction.

The carriage 52 is supported on the X-axis direction rail 51 via rollers (not shown). The carriage 52 is able to move, under control of the controller 6 or a manual operation, in the X-axis direction along the X-axis direction rail 51.

The X-axis direction rail 51 supporting the carriage 52 is able to slide along the Z-axis direction rail R2 in the Z-axis direction. The carriage 52 is able to slide along the X-axis direction rail 51 in the X-axis direction. Therefore, the carriage 52 is able to slide in the surgical operation room in the horizontal direction (X-axis direction and Z-axis direction).

The operation room display device 53 is rotatably supported by the carriage 52 via rollers (not shown). The operation room display device 53 is able to move, under control of the controller 6 or a manual operation, in the vertical axis rotating direction. That is, the operation room display device 53 is able to rotate in the vertical axis rotating direction. The operation room display device 53 displays the X-ray image such as a fluoroscopic image and a radiographic image together with character information and scales of various parameters. As the operation room display device 53, a display device such as a liquid crystal display may be used.

The controller 6 includes processing circuitry (not shown) and a memory (not shown). The controller 6 is a control circuit that performs, under control of the image processing apparatus 9, conditioning for operating the movable device and conditioning for performing an X-ray imaging. For example, the movable device includes the X-axis direction rail 21, the carriage 22, the vertical axis rotating device 23 (or the suspension arm 24), the C-arm rotating device 25, the C-arm 26, the X-ray emitting device 27, the X-ray detecting device 28, the bed main body 41, the table 42, the X-axis direction rail 51, the carriage 52, the operation room display device 53, and the like. When the X-ray imaging system 1A is a biplane type system including two X-ray emitting devices 27 and the like, each of these devices is the movable device.

Further, the controller 6 acquires encoder data from a rotary encoder E (shown in FIG. 3) attached to a roller (not shown) of the movable device such as the C-arm 26. The controller 6 calculates, based on the acquired encoder data, arrangement data (position and angle) on the movable device, and transmits it to the image processing apparatus 9. The rotary encoder E is a sensor which converts the mechanical displacement amount of the rotation of the roller, moving the movable device, into an electric signal and processes the electric signal, thereby detecting the encoder data which is the basis of the arrangement data on the movable device.

For example, the controller 6 calculates the arrangement data of the C-arm 26, based on the encoder data of the X-axis direction rail 21 (a position of the X-axis direction rail 21 with respect to the Z-axis direction rail R1), on the encoder data of the carriage 22 (a position of the carriage 22 with respect to the X-axis direction rail 21), on the encoder data of the vertical axis rotating device 23 or the suspension arm 24 (a position of the vertical axis rotating device 23 with respect to the carriage 22), on the encoder data of the C-arm rotating device 25 (a position of the C-arm rotating device 25 with respect to the suspension arm 24), and on the C-arm 26 (a position of the C-arm 26 with respect to the C-arm rotating device 25).

For example, the controller 6 calculates the arrangement data of the X-ray emitting device 27, based on the encoder data of the X-axis direction rail 21 (a position of the X-axis direction rail 21 with respect to the Z-axis direction rail R1), on the encoder data of the carriage 22 (a position of the carriage 22 with respect to the X-axis direction rail 21), on the encoder data of the vertical axis rotating device 23 or the suspension arm 24 (a position of the vertical axis rotating device 23 with respect to the carriage 22), on the encoder data of the C-arm rotating device 25 (a position of the C-arm rotating device 25 with respect to the suspension arm 24), on the C-arm 26 (a position of the C-arm 26 with respect to the C-arm rotating device 25), and on the encoder data of the X-ray emitting device 27 (a position of the X-ray emitting device 27 with respect to the C-arm 26).

For example, the controller 6 calculates the arrangement data of the X-ray detecting device 28, based on the encoder data of the X-axis direction rail 21 (a position of the X-axis direction rail 21 with respect to the Z-axis direction rail R1), on the encoder data of the carriage 22 (a position of the carriage 22 with respect to the X-axis direction rail 21), on the encoder data of the vertical axis rotating device 23 or the suspension arm 24 (a position of the vertical axis rotating device 23 with respect to the carriage 22), on the encoder data of the C-arm rotating device 25 (a position of the C-arm rotating device 25 with respect to the suspension arm 24), on the C-arm 26 (a position of the C-arm 26 with respect to the C-arm rotating device 25), and on the encoder data of the X-ray detecting device 28 (a position of the X-ray detecting device 28 with respect to the C-arm 26).

For example, the controller 6 calculates the arrangement data of the table 42, based on the encoder data of the bed main body 41 (a height position the upper part of the bed main body 41 with respect to the floor), and on the encoder data of the table 42 (a position of the table 42 with respect to the upper part of the bed main body 41).

For example, the controller 6 calculates the arrangement data of the operation room display device 53, based on the encoder data of the X-axis direction rail 51 (a position of the X-axis direction rail 51 with respect to the Z-axis direction rail R2), on the encoder data of the carriage 52 (a position of the carriage 52 with respect to the X-axis direction rail 51), and on the encoder data of the operation room display device 53 (a position of the operation room display device 53 with respect to the carriage 52).

The operation room input circuit 7 is a circuit for inputting an operation signal from an input device (keyboard, mouse, etc.) which is able to be operated mainly by the operator such as an assistant or the like. Here, it is assumed that the input device itself is also included in the operating room input circuit 7. The operating room input circuit 7 transmits the operation signal to the controller 6.

The wearable device 8A includes, as shown in FIGS. 2A to 2C, a structure which is wearable by the operator D.

Each of FIGS. 2A and 2B is a diagram showing a configuration example of the wearable device 8A arranged in the X-ray imaging system 1A. FIG. 2C is a diagram showing a worn state of the wearable device 8A.

The wearable device 8A includes, as shown in FIGS. 2A to 2C, a sensor 81 and a transmissive type display device 82A The sensor 81 detects its own position, that is, a sensor position P [x, y, z], and its own direction (two deflection angles θ and φ), that is, a sensor direction F. For example, when the sensor 81 detects at least two sensor positions, the sensor direction F can be detected from the detection results of the at least two positions. The sensor 81 detects magnitude and direction of the magnetic field generated by a magnetic field generator (not shown), and detects the sensor position P and the sensor direction F based on the magnitude and direction of the detected magnetic field. Note that the sensor 81 may be a so-called nine-axis sensor. The nine-axis sensor includes at least one of a triaxial gyro sensor which detects angular velocities of three axes in a three-dimensional space, a three-axis acceleration sensor which detects accelerations of three axes in a three-dimensional space, three-axis geomagnetism in a three-dimensional space, and a three-axis terrestrial magnetism sensor which detects the geomagnetic field.

The sensor 81 transmits position data and attitude data of the wearable device 8A to the image processing apparatus 9 (shown in FIG. 3). The position data of the wearable device 8A may be the sensor position P detected by the sensor 81 or a reference position PA to be described later. The attitude data of the wearable device 8A is the sensor direction F detected by the sensor 81. The wearable device 8A and the image processing apparatus 9 may be connected so as to be capable of wired communication, or may be connected so as to enable wireless communication. When the wearable device 8A and the image processing apparatus 9 are connected so as to be wirelessly communicable with each other, a configuration for performing short range communication (Near Field Communication) such as Bluetooth® or WiFi is provided.

The transmissive type display device 82A has a structure capable of displaying parallax images for stereoscopic viewing. The transmissive type display device 82A includes one or two displays for displaying parallax images. In the case where the transmissive type display device 82A includes one display, the display is an eyeglass type 3D display employing an anaglyph method, a polarizing method, a liquid crystal shutter method, or the like. Alternatively, when the transmissive type display device 82A includes one display, the display is a glassless type 3D display employing a parallax barrier method, an integral (lenticular lens) method, or the like. Hereinafter, a case where the transmissive type display device 82A includes two displays will be described.

The transmissive type display device 82A includes a transmissive type display DLA for the left-eye and a transmissive type display DRA for the right-eye. Each of the transmissive type displays DLA and DRA means a display having a structure capable of displaying an image (parallax image to be described later), and a structure capable of seeing thorough outside from inside.

A reference position PA is set, as shown in FIG. 2A, at a position distant from the sensor position P by a distance q (q is a preset value). The reference position PA is set as the intermediate position between the left-eye PL and the right-eye PR of the operator D who wears the wearable device 8A. The reference position PA is separated by a distance u (u is a preset value) from each of the left-eye PL and the right-eye PR of the operator D who wears the wearable device 8A. The reference position PA, the position of the left-eye PL, and the position of the right-eye PR are used in specifying a blind area in FIGS. 5A and 5B to be described later. The blind area means, when an observation area with the position of the wearable device 8A is set as a base point, an area showing a three-dimensional model element included in the observation area, and the three-dimensional model element being different from a three-dimensional model element closest to the base point.

Returning to the explanation of FIG. 1, the image processing apparatus 9 is configured on the basis of a computer, the image processing apparatus 9 controls the overall operation of the X-ray imaging system 1A and performs image processing on the X-ray image acquired by the first holding device 2. The image processing apparatus 9 includes processing circuitry 91, a memory (or storage) 92, an X-ray image generating circuit 93, an X-ray image processing circuit 94, a control room display device 95, and a control room input circuit 96.

The processing circuitry 91 means any one of dedicated or general central processing unit (CPU) and a micro processor unit (MPU), an application specific integrated circuit (ASIC), and a programmable logic device. The programmable logic device may be, for example, any one of a simple programmable logic device (SPLD), a complex programmable logic device (CPLD), a field programmable gate array (FPGA) and the like. The processing circuitry 91 realizes functions to be described later by reading out and executing a program stored in the memory 92 or directly incorporated in the processing circuitry 91.

The processing circuitry 91 may be a single processing circuit or a combination of multiple processing circuits. In the latter case, the memory 92 includes multiple memory elements each storing an element of a program that the processing circuitry 91 executes, and each corresponding to the processing circuit. Alternatively, in the latter case, the memory 92 includes a single memory storing the program that the processing circuitry 91 executes, and corresponding to the multiple processing circuits.

The memory 92 includes a semiconductor memory element such as a random access memory (RAM), a flash memory and the like, a hard disk, an optical disk and the like. The memory 92 may be a portable media such as a universal serial bus (USB) memory, a digital video disk (DVD) and the like. The memory 92 stores various processing programs (in addition to application programs, an operating system (OS) and the like are also included), data required for execution of the programs, the image data, and a three-dimensional model of an observation target device (movable device and fixed device) described later. The OS may include a graphical user interface (GUI) which enables basic operations by the control room input circuit 96 by using many graphics in display of the image on the control room display device 95 to the operator.

The X-ray image generating circuit 93 performs a logarithmic transformation process (LOG process) on the projection data output from the X-ray detecting device 28 of the first holding device 2, and performs, if necessary, an addition process, thereby generating X-ray image data, under control of the processing circuitry 91. The X-ray image generating circuit 93 is an example of X-ray image generating unit.

The X-ray image processing circuit 94 performs an image processing on the X-ray image generated by the X-ray image generating circuit 93, under control of the processing circuitry 91. The image processing may include an enlargement processing, a gradation processing, or a spatial filter processing on data. The image processing may include a minimum/maximum value tracing processing of data accumulated in time series, an addition processing for removing noise, or the like. Data after the image processing by the X-ray image processing circuit 94 is output to the operation room display device 53 and the control room display device 95, and stored in the memory 92. The X-ray image processing circuit 94 is an example of X-ray image processing unit.

The control room display device 95 displays the X-ray image together with the character information of various parameters, scale, and the like. As the control room display device 95, a display device such as the liquid crystal display can be used like the operation room display device 53.

The control room input circuit 96 is a circuit for inputting an operation signal from an input device (a keyboard, a mouse, etc.) which is able to be operated by the operator. Here, it is assumed that the input device itself is also included in the control room input circuit 96. The control room input circuit 96 transmits the operation signal to the processing circuitry 91.

FIG. 3 is a block diagram showing functions of the X-ray imaging system 1A.

As the processing circuitry 91 executes a program, the X-ray imaging system 1A achieves a movable device data acquiring function 91a, a three-dimensional model acquiring function 91b, a three-dimensional model arranging function 91c, a wearable device data acquiring function 91d, an image generating function 91e, and an X-ray imaging function 91f. It is to be noted that the functions 91a to 91f are achieved by executing the program, but it is not limited to that case. All or a part of the functions 91a to 91f may be achieved as a circuit such as the ASIC in the X-ray imaging system 1A.

The movable device data acquiring function 91a is a function of acquiring, from the controller 6, arrangement data on the movable device. For example, the movable device data acquiring function 91a is a function of acquiring arrangement data on the movable device such as the C-arm 26.

The three-dimensional model acquiring function 91b is a function of acquiring, from the memory 92, a three-dimensional model relating to the observation target device. For example, the three-dimensional model acquiring function 91b is a function of acquiring a three-dimensional model relating to the movable device such as the C-arm 26.

The three-dimensional model arranging function 91c is a function of arranging the three-dimensional model, relating to the observation target device acquired by the three-dimensional model acquiring function 91b, in the virtual space. For example, the three-dimensional model arranging function 91c arranges a three-dimensional model relating to the observation target device in the virtual space, in accordance with known invariant arrangement data on the fixed device and the arrangement data on the movable device acquired by the movable device data acquiring function 91a.

The wearable device data acquiring function 91d is a function of acquiring, from the wearable device 8A, the position data and the attitude data on the operator D, that is, the wearable device 8A.

The image generating function 91e is a function of acquiring data indicating a relative positional relationship between the operator D and the observation target device, and of generating an image of the three-dimensional model included in a blind area when viewed from the operator D, based on the data indicating the positional relationship and the three-dimensional model arranged in the virtual space by the three-dimensional model arranging function 91c. Specifically, when viewing the three-dimensional model arranged in the virtual space by the three-dimensional model arranging function 91c in accordance with the position data and the attitude data of the wearable device 8A, the image generating function 91e specifies, as the blind area, an area existing in a blind spot in the three-dimensional model, generates the image including the blind area as parallax images, and transmits the parallax images including the blind area to the wearable device 8A. Details will be described later with reference to FIGS. 5A to 5C.

The transmissive type display DLA (shown in FIG. 2) for the left-eye and the transmissive type display DRA (shown in FIG. 2) for the right-eye of the transmissive type display device 82A display the transmitted parallax images, respectively.

The X-ray imaging function 91f is a function of controlling the controller 6, the X-ray image generating circuit 93 and the X-ray image processing circuit 94 shown in FIG. 1 and the like to execute X-ray imaging, thereby generating an X-ray image. The X-ray imaging function 91f is a function of displaying the X-ray image on the display devices 53 and 95 (shown in FIG. 1) or storing them in the memory 92.

Subsequently, an operation of the X-ray imaging system 1A will be described with reference to FIGS. 3 and 4. Unless otherwise mentioned, the case where the observation target device includes the C-arm 26, the X-ray emitting device 27, the X-ray detecting device 28, the bed main body 41, and the table 42 and does not include the fixing device will be described. Note that the observation target device may include, when the X-ray imaging system 1A includes an X-ray CT (Computed Tomography) device, a housing unit (also called "gantry device") as a fixing device in addition to the movable device.

FIG. 4 is a flowchart showing an example of the operation of the X-ray imaging system 1A.

In accordance with the operation by the operator, the controller 6 to transmit the operate signal to the movable device such as the C-arm 26, the X-ray emitting device 27, the X-ray detecting device 28, the bed main body 41, or the table 42, to control the movement of the movable devices. The controller 6 acquires the encoder data from the rotary encoder E according to the movement of the movable device, and calculates the arrangement data on the movable device such as the C-arm 26 (step ST1).

The movable device data acquiring function 91*a* acquires the arrangement data on the movable device such as the C-arm 26 from the controller 6 (step ST2).

The three-dimensional model acquiring function 91*b* acquires a three-dimensional model relating to the movable device such as the C-arm 26 from the memory 92 (step ST3).

The three-dimensional model arranging function 91*c* arranges, according to the arrangement data on the movable device acquired in step ST2, the three-dimensional model relating to the movable device such as the C-arm 26, acquired in step ST3, in the virtual space (step ST4).

The sensor 81 of the wearable device 8A detects its own position data and attitude data, that is, position data and attitude data on the wearable device 8A (step ST5).

The wearable device data acquiring function 91*d* acquires the position data and the attitude data on the wearable device 8A, detected in step ST5, from the wearable device 8A (step ST6).

The image generating function 91*e* specifies, when viewing the three-dimensional model arranged in the virtual space in accordance with the position data and the attitude data of the wearable device 8A in step ST4, an area existing in a blind spot in the three-dimensional model as the blind area. The image generating function 91*e* generates the parallax images including the blind area (step ST7). The image generating function 91*e* transmits the parallax images including the blind area to the wearable device 8A.

Here, the image generating function 91*e* may recognize the blind spot in units of one element included in the three-dimensional model, or may recognize the blind spot in units of a set of multiple elements included in the three-dimensional model, thereby specifying the blind area. In the former case, for example, the image generating function 91*e* recognizes the blind spot caused by each of the five elements relating to the C-arm 26, the X-ray emitting device 27, the X-ray detecting device 28, the bed main body 41, and the table 42. In the latter case, for example, the image generating function 91*e* recognizes the blind spot caused by each of a C-arm device and the bed device 4, the C-arm device including three elements relating to the C-arm 26, the X-ray emitting device 27 and the X-ray detecting device 28, the bed device 4 including two elements relating to the bed main body 41 and the table 42. Hereinafter, the latter case will be described with reference to FIGS. 5A to 5C and FIGS. 10A to 10C.

FIG. 5A is a diagram for explaining a method of setting the position data of the wearable device 8A. FIG. 5B is a diagram for explaining a method of specifying the blind area. FIG. 5C is a diagram for explaining a method of generating the parallax images including the blind area.

FIGS. 5A to 5C illustrate a process for displaying, on the transmissive type display in front of both eyes of the operator D, the blind area of the virtual space at an appropriate position and an appropriate size. It follows that the blind area of the virtual space appears, when the operator D (shown in FIG. 2C) wearing the wearable device 8A looks at a blind spot part of the real space, at the blind spot part of the real space.

As shown in FIG. 5A, a reference position PA [xa, ya, za] of the wearable device 8A is expressed, based on the sensor position P [x, y, z] and the sensor direction F, and a distance q between the reference position pp, and the sensor position P, as PA [x+q×sin θ cos φ, y+q×sin θ sin φ, z+q×cos θ].

The positions of the left-eye PL and the right-eye PR of the operator D who wears the wearable device 8A are set based on the reference position PA which is the intermediate position between them, a distance u (shown in FIG. 2C) from the reference position PA, and the sensor direction F.

Next, in the virtual space of the X'Y'Z' system shown in FIG. 5B, three-dimensional model elements 26 to 28 relating to the C-arm device and three-dimensional model elements 41 to 42 relating to the bed device 4 are arranged. X'Y'Z' axes of the virtual space correspond to XYZ axes of the real space, respectively. In the virtual space, an observation position PA' of the virtual space and an observation direction F' of the virtual space are set, the observation position PA' corresponding to the reference position PA (shown in FIG. 5A) of the real space, the observation direction F' corresponding to the sensor direction F (shown in FIG. 2C) of the real space. An observation angle α (α is a preset value) around the observation direction F' is set in the virtual space. In the virtual space, a surface W is set, the surface W being located at a distance r (r is a preset value) from the observation position PA' along the observation direction F', and the surface W being orthogonal to the observation direction F', and the surface W being formed by an observation angle α having the observation direction F' as a base point. A conical or quadrangular pyramidal observation area IA is set in the virtual space, the observation area IA being formed by multiple straight lines (for example, straight lines V1 to V3) connecting the observation position PA' and each point on the surface W.

In the virtual space shown in FIG. 5B, straight lines (for example, straight lines V2 and V3) are extracted of the multiple straight lines in the observation area IA, the extracted straight lines passing thorough both of the three-dimensional model of the C-arm device, including the three-dimensional model elements 26 to 28, and of the three-dimensional model of the bed device 4, including the three-dimensional model elements 41 to 42. In the extracted straight lines, the three-dimensional model elements 41 to 42 related to the bed device 4 closest to the observation position PA' are specified. An area indicating the three-dimensional model elements 26 to 28 relating to the C-arm device different from the specified three-dimensional model elements 41 to 42 is specified as a blind area N (shown in FIG. 5C). The existence of a straight line passing through multiple three-dimensional model elements means that the second observation target device exists in the blind spot caused by the first observation target device, when viewed from the operator D at the present position.

Next, in the virtual space shown in FIG. 5C, a projection direction FL for the left-eye is set, the projection direction FL extending from the position of a left-eye PL' of the virtual space, corresponding to the position of the left-eye PL of the real space, to the center of the surface W. A projection direction FR for the right-eye is set, the projection direction FR extending from the position of a right-eye PR' of the virtual space, corresponding to the position of the right-eye PR of the real space, to the center of the surface W. Each of the eyes PL' and PR' of the virtual space is separated from the observation position PA' of the virtual space, by a distance u' of the virtual space corresponding to the distance u (shown in FIG. 2C) of the real space.

In the virtual space shown in FIG. 5C, projection processing (surface rendering processing, volume rendering processing or the like) of an area including the blind area N is performed toward a left-eye projection plane GL orthogonal to the projection direction FL for the left-eye, using the position of the left-eye PL' of the virtual space as a viewpoint. As a result, a left-eye image including the blind area N is generated on the left-eye projection plane GL. Similarly, in the virtual space, the projection processing of an area including the blind area N is performed toward a right-eye projection plane GR orthogonal to the projection direction FR for the right-eye, using the position of the right-eye PR' of the virtual space as a viewpoint. As a result, a right-eye image including the blind area N is generated on the right-eye projection plane GR.

Note that the left-eye projection plane GL in the virtual space shown in FIG. 5C is located at a position separated by a distance t' of the virtual space corresponding to a distance t (shown in FIG. 2C, t is a preset value), from the position of the left-eye PL' which is the viewpoint of projection processing. The distance t is a distance between the position of the left-eye PL of the operator D who wears the wearable device 8A and the transmissive type display DLA for the left-eye (shown in FIG. 2C). Similarly, the right-eye projection plane GR in the virtual space is located at a position separated by the distance t' of the virtual space, from the position of the right-eye PR' which is the viewpoint of projection processing. With such a setting, the sizes of the parallax images projected on the projection planes GL and GR can be matched with the sizes of the transmissive type displays DLA and DRA.

It is preferable that projection angles of the virtual space is matched with viewing angles of the real space via the transmissive type displays DLA and DRA of the operator D, respectively, who wears the wearable device 8A. The projection angles of the virtual space is formed by the position of the eye PL' and the plane W, and by the position of the eye PR' and the plane W, respectively, the two eyes PL' and PR' being the viewpoints in the virtual space. In order to realize this, the observation angle α and the distance r which are arbitrarily set are adjusted.

Returning to the explanation of FIGS. 3 and 4, the left-eye transmissive type display DLA (shown in FIG. 2C) of the transmissive type display device 82A displays the left-eye image including the blind area, the right-eye transmissive type display DRA (shown in FIG. 2C) displays the right-eye image including the blind area (step ST8). When displaying the parallax images, the transmissive type display device 82A may adjust the centers of the parallax images to the centers of the transmissive type displays DLA and DRA, respectively.

FIG. 6A is a schematic diagram showing a field of view of an operator in the prior art. FIG. 6B is a diagram showing parallax images displayed on the transmissive type displays DLA and DRA of the wearable device 8A. FIG. 6C is a schematic diagram showing a field of view of the operator D wearing the wearable device 8A in the X-ray imaging system 1A.

As shown in FIG. 6A, when viewed from an operator, a part of the C-arm 26 exists at a blind spot caused by the table 42 or the subject S, the C-arm 26 and the table 42 being the movable device. When rotating the C-arm 26, the tip of the C-arm 26 (X-ray emitting device or X-ray detecting device) may collide with the bed main body 41 or the table 42 at a blind spot. Therefore, the operator needs an excessive burden during the operation.

Therefore, as shown in FIG. 6B, the parallax images including the blind area N are displayed on the transmissive type displays DLA and DRA of the wearable device 8A, respectively, worn by the operator D. That is, a portion of the three-dimensional model element is displayed on the transmissive type displays DLA and DRA of the wearable device 8A. The part of the three-dimensional model element relates to a part of the C-arm device, the part existing in the blind spot caused by the table 42 as viewed from the operator D. As a result of such display, as shown in FIG. 6C, an image appears in the field of view of the operator D wearing the wearable device 8A, the image showing the portion of the C-arm 26 and the portion of the X-ray emitting device 27 in the blind spot caused by the table 42. Therefore, the burden on the operator D when rotating the C-arm 26 is reduced.

Returning to the explanation of FIGS. 3 and 4, the movable device data acquiring function 91a determines whether or not the display of the parallax images, that is, the blind spot display in step ST8 is finished (step ST9). If it is determined as "YES" in step ST9, that is, if it is determined that the blind spot display is finished, the X-ray imaging function 91f controls, in accordance with an instruction of an X-ray imaging, the X-ray image generating circuit 93, the X-ray image processing circuit 94, and the like, thereby performing the X-ray imaging (step ST10).

If it is determined as "NO" in step ST9, that is, if it is determined that the blind spot display is not finished, the movable device data acquiring function 91a acquires, at the next timing, the arrangement data on the movable device such as the C-arm 26 (step ST2).

Although the X-ray imaging system 1A has been described as performing the blind spot display in step ST8 before the X-ray imaging in step ST10, it is not limited to that case. For example, the X-ray imaging system 1A may perform the blind spot display during the X-ray imaging or may perform the blind spot display after the X-ray imaging.

It is possible to display, when the X-ray imaging system LA performs the above-described blind spot display, an area invisible from the operator D in the real space, using the parallax images generated in the virtual space. The displayed parallax images are acquired by projecting the blind area, specified in the virtual space, onto the surfaces of the transmissive type displays DRA and DLA in the real space.

According to the X-ray imaging system 1A, it is possible to display, even if the position of the blind spot varies according to the movement of the operator D, (A) the movable device existing in the blind spot caused by the fixed device, (B) the fixed device existing in the blind spot caused by the movable device, and (C) the first movable device existing in the blind spot caused by the second movable device. This is because it is unnecessary to optically image the blind spot that occurs when viewed from the operator D.

That is, according to the X-ray imaging system 1A, it is possible to improve, when there is the observation target device including at least one movable device movable independently, operability of the movable device by the operator D.

2. Second Embodiment of Image Displaying System 1

The overall configuration of an X-ray imaging system 1B according to a second embodiment is the same as, except for the replacement of the wearable device 8A with a wearable device 8B, that of the X-ray imaging system 1A, the wearable device 8A being included in the X-ray imaging system 1A according to the first embodiment shown in FIG. 1. For that reason, the description of the configuration of the X-ray imaging system 1B will be omitted. In the X-ray imaging system 1A according to the first embodiment, the wearable device 8A including the transmissive type display device 82A is used. On the other hand, in the X-ray imaging system 1B according to the second embodiment, the wearable device 8B including the non-transmissive type display device 82B is used.

Each of FIGS. 7A and 7B is a diagram showing a configuration example of the wearable device 8B arranged in the X-ray imaging system 1B. FIG. 7C is a diagram showing a worn state of the wearable device 8B. In FIGS. 7A to 7C, same reference numerals are given to same members as those shown in FIGS. 2A to 2C, and the explanation will be omitted.

As shown in FIGS. 7A to 70, the wearable device 8B includes a sensor 81, a non-transmissive type display device 82B, and an optical imaging device 83B.

The sensor 81 transmits the position data and the attitude data of the wearable device 8B to the image processing device 9 (shown in FIG. 8). The position data of the wearable device 8B may be the sensor position P detected by the sensor 81 or may be a reference position PB to be described later. The attitude data of the wearable device 8B is the sensor direction F detected by the sensor 81. It is to be noted that the wearable device 8B and the image processing device 9 may be connected so as to be capable of wired communication, or may be connected so as to enable wireless communication.

The non-transmissive type display device 82B has a structure capable of displaying parallax images for stereoscopic viewing. The non-transmissive type display device 82B includes one or two displays for displaying parallax images. In the case where the non-transmissive type display device 82B includes one display, the display is an eyeglass type 3D display employing an anaglyph method, a polarizing method, a liquid crystal shutter method, or the like. Alternatively, when the non-transmissive type display device 82B includes one display, the display is a glassless type 3D display employing a parallax barrier method, an integral (lenticular lens) method, or the like. Hereinafter, a case where the non-transmissive type display device 82B includes two displays will be described.

The non-transmissive type display device 82B includes a non-transmissive type display DLB for the left-eye and a non-transmissive type display DRB for the right-eye. Each of the non-transmissive type displays DLB and DRB means a display having a structure capable of displaying an image (parallax images to be described later), and a structure not capable of seeing thorough its back side via itself.

The optical imaging device 83B includes a left-eye camera CL and a right-eye camera CR for performing an optical imaging and acquiring parallax images for stereoscopic viewing. The parallax images acquired by the left-eye camera CL and the right-eye camera CR are transmitted to the non-transmissive type displays DLB and DRB.

As shown in FIG. 7A, the reference position PB is set at a position separated from the sensor position P by a distance k (k is a preset value). The reference position PB is set as the intermediate position between the left-eye camera CL and the right-eye camera CR of the wearable device 8B. The reference position PB is separated by a distance m (m is a preset value) from the left-eye camera CL and the right-eye camera CR of the wearable device 8B. The reference position PB, the position of the camera CL for the left-eye, and the position of the camera CR for the right-eye are used in specifying a blind area in FIGS. 10A and 10B to be described later.

FIG. 8 is a block diagram showing functions of the X-ray imaging system 1B.

As the processing circuitry 91 executes the program, the X-ray imaging system 1B achieves a movable device data acquiring function 91a, a three-dimensional model acquiring function 91b, a three-dimensional model arranging function 91c, a wearable device data acquiring function 91d, an image generating function 91e, and an X-ray imaging function 91f. It is to be noted that the functions 91a to 91f are achieved by executing the program, but it is not limited to that case. All or a part of the functions 91a to 91f may be achieved as a circuit such as the ASIC in the X-ray imaging system 1B.

In FIG. 8, same reference numerals are given to same members as those shown in FIG. 3, and the explanation will be omitted.

The wearing device data acquiring function 91d is a function of acquiring the position data and the attitude data on the wearable device 8B from the wearable device 8B.

When viewing the three-dimensional model arranged in the virtual space by the three-dimensional model arranging function 91c in accordance with the position data and the attitude data of the wearable device 8B, the image generating function 91e specifies, as the blind area, an area existing in a blind spot in the three-dimensional model. The image generating function 91e generates the image including the blind area as parallax images. The image generating function 91e transmits the parallax images including the blind area to the wearable device 8B. Details will be described later with reference to FIGS. 10A to 10C.

The non-transmissive type display DLB for the left-eye (shown in FIG. 7) and the non-transmissive type display DRB for the right-eye (shown in FIG. 7) of the non-transmissive type display device 82B display the transmitted parallax images, respectively.

Subsequently, an operation of the X-ray imaging system 1B will be described with reference to FIGS. 8 and 9. Unless otherwise mentioned, when arranging the three-dimensional model relating to the observation target device, a case where the three-dimensional model arranging function 91c does not arrange the three-dimensional model relating to the fixed device, and arranges the three-dimensional model relating to the C-arm 26, the X-ray emitting device 27, the X-ray detecting device 28, the bed main body 41, and the table 42 will be described.

FIG. 9 is a flowchart showing an example of an operation of the X-ray imaging system 1B. In FIG. 9, same reference numerals are given to same steps as those shown in FIG. 4, and the explanation will be omitted.

The sensor 81 of the wearable device 8B detects its own position data and attitude data, that is, position data and attitude data on the wearable device 8B (step ST15).

The wearable device data acquiring function 91d acquires the position data and the attitude data on the wearable device 8B, detected in step ST15, from the wearable device 8B (step ST16).

The image generating function 91e specifies, when viewing the three-dimensional model arranged in the virtual space in accordance with the position data and the attitude data of the wearable device 8B in step ST4, an area existing in a blind spot in the three-dimensional model as the blind area. The image generating function 91e generates the parallax images including the blind area (step ST17). The image generating function 91e transmits the parallax images including the blind area to the wearable device 8B.

FIG. 10A is a diagram for explaining a method of setting the position data of the wearable device 8B. FIG. 10B is a diagram for explaining a method of specifying the blind area. FIG. 10C is a diagram for explaining a method of generating the parallax images including the blind area.

FIGS. 10A to 10C illustrate a process for displaying, on the non-transmissive type display in front of both eyes of the operator D, the blind area of the virtual space at an appropriate position and an appropriate size. It follows that the blind area of the virtual space appears, when the operator D (shown in FIG. 7C) wearing the wearable device 8B looks at a blind spot part of the real space, at the blind spot part of the real space.

As shown in FIG. 10A, a reference position PB [xb, yb, zb] of the wearable device 8B is expressed, based on the sensor position P [x, y, z] and the sensor direction F, and a distance k between the reference position PB and the sensor position P, as PB [x+k×sin θ cos φ, y+k×sin θ sin φ, z+k×cos θ].

The positions of the left-eye camera CL and the right-eye camera CR of the wearable device 8B are set based on the reference position PB which is the intermediate position between them, a distance m (shown in FIG. 7C) from the reference position PB, and the sensor direction F.

Next, in the virtual space of the X'Y'Z' system shown in FIG. 10B, three-dimensional model elements 26 to 28 relating to the C-arm device and three-dimensional model elements 41 to 42 relating to the bed device 4 are arranged. X'Y'Z' axes of the virtual space correspond to XYZ axes of the real space, respectively. In the virtual space, an observation position PB' of the virtual space and an observation direction F' of the virtual space are set, the observation position PB' corresponding to the reference position PB (shown in FIG. 10A) of the real space, the observation direction F' corresponding to the sensor direction F (shown in FIG. 7C) of the real space. An observation angle α (α is a preset value) around the observation direction F' is set in the virtual space. In the virtual space, a surface W is set, the surface W being located at a distance r (r is a preset value) from the observation position PB' along the observation direction F', and the surface W being orthogonal to the observation direction F', and the surface W being formed by an observation angle α having the observation direction F' as a base point. A conical or quadrangular pyramidal observation area IB is set in the virtual space, the observation area IB being formed by multiple straight lines (for example, straight lines V1 to V3) connecting the observation position PB' and each point on the surface W.

In the virtual space shown in FIG. 10B, straight lines (for example, straight lines V2 and V3) are extracted of the multiple straight lines in the observation area IB, the extracted straight lines passing thorough both of the three-dimensional model of the C-arm device, including the three-dimensional model elements 26 to 28, and of the three-dimensional model of the bed device 4, including three-dimensional model elements 41 to 42. In the extracted straight lines, the three-dimensional model elements 41 to 42 related to the bed device 4 closest to the observation position PB' are specified. An area indicating the three-dimensional model elements 26 to 28 relating to the C-arm device different from the specified three-dimensional model elements 41 to 42 is specified as a blind area N (shown in FIG. 10C). The existence of a straight line passing through multiple three-dimensional model elements means that the second observation target device exists in the blind spot caused by the first observation target device, when viewed from the operator D at the present position.

That is, in FIGS. 5A to 5C, when the operator D directly views the observation target device with both eyes, the parallax images including the blind area is displayed on the displays DLA and DRA in front of both eyes. Therefore, the intermediate position PA (shown in FIG. 2C) between the two eyes is the reference position. On the other hand, in FIGS. 10A to 10C, when the operator D indirectly views the observation target device through the parallax images displayed on the displays DLB and DRB in front of both eyes, blind area images are respectively superimposed on the camera images displayed on displays DLB and DRB. Therefore, the intermediate position PB (shown in FIG. 7C) of the cameras CL and CR is the reference position.

Next, in the virtual space shown in FIG. 10C, a projection direction FL for the left-eye is set, the projection direction FL extending from the position of a left-eye camera CL' of the virtual space, corresponding to the position of the left-eye camera CL of the real space, to the center of the surface W. A projection direction FR for the right-eye is set, the projection direction FR extending from a position of the right-eye camera CR' of the virtual space, corresponding to the position of the right-eye camera CR of the real space, to the center of the surface W. Each of the cameras CL' and CR' of the virtual space is separated from the observation position PB' of the virtual space, by a distance m' of the virtual space corresponding to the distance m (shown in FIG. 7C) of the real space.

In the virtual space shown in FIG. 10C, projection processing of an area including the blind area N is performed toward a left-eye projection plane GL orthogonal to the projection direction FL for the left-eye, using the position of the left-eye camera CL' of the virtual space as a viewpoint. As a result, a left-eye image including the blind area N is generated on the left-eye projection plane GL. Similarly, in the virtual space, the projection processing of an area including the blind area N is performed toward a right-eye projection plane GR orthogonal to the projection direction FR for the right-eye, using the position of the right-eye camera CR' of the virtual space as a viewpoint. As a result, a right-eye image including the blind area N is generated on the right-eye projection plane GR.

Note that the left-eye projection plane GL in the virtual space shown in FIG. 10C is located at a position separated by a distance j' of the virtual space corresponding to a focal length (preset value) of the left-eye camera CL, from the position of the left-eye camera CL' which the viewpoint of projection processing. Similarly, the right-eye projection plane GR in the virtual space is located at a position separated by the distance j' of the virtual space, from the position of the right-eye camera CR' which is the viewpoint of projection processing. With such a setting, the sizes of the parallax images, projected on the projection planes GL and GR, including the blind area can be matched with the sizes of the parallax images based on the optical imaging.

It is preferable that projection angles of the virtual space is matched with viewing angles of the cameras CL' and CR'. In order to realize this, the observation angle α and the distance r which are arbitrarily set are adjusted.

Returning to the explanation of FIGS. 8 and 9, the left-eye camera CL and the right-eye camera CR of the optical imaging device 83B perform the optical imaging and acquire parallax images by the optical imaging (step ST18).

The non-transmissive type display DLB (shown in FIG. 7C) for the left-eye of the non-transmissive display type device 82B superimposes the left-eye image including the blind area transmitted, with the left-eye image by the left-eye camera CL acquired in step ST18, thereby generating and displaying the superimposed left-eye image. The non-transmissive type display DRB (shown in FIG. 7C) for the right-eye superimposes the right-eye image including the blind area transmitted, with the right-eye image by the right-eye camera CR acquired in step ST18, thereby generating and displaying the superimposed right-eye image (step ST19). When displaying the superimposed parallax images, the non-transmissive type display device 82B may adjust the centers of the parallax images including the blind area to the centers of the parallax images by the optical imaging, respectively.

FIG. 11 is a diagram showing parallax images displayed on the non-transmissive type displays DLB and DRB of the wearable device 8B.

As shown in FIG. 11, the superimposed images including the blind area N are displayed on the non-transmissive type displays DLB and DRB of the wearable device 8B, respectively, worn by the operator D. That is, a portion of the three-dimensional model element is displayed on the non-transmissive type displays DLB and DRB of the wearable device 8A. The part of the three-dimensional model element relates to a part of the C-arm device, the part existing in the blind spot caused by the table 42 as viewed from the operator D. As a result of such display, an image appears in the field of view of the operator D wearing the wearable device 8B, the image showing the portion of the C-arm 26 in the blind spot caused by the table 42. Therefore, the burden on the operator D when rotating the C-arm 26 is reduced.

The non-transmissive type displays DLB and DRB may arbitrarily adjust the transparency of the parallax images including the blind area to be superimposed on the parallax images by the optical imaging.

Although the X-ray imaging system 1B has been described as performing the blind spot display in step ST19 before the X-ray imaging in step ST10, it is not limited to that case. For example, the X-ray imaging system 1B may perform the blind spot display during the X-ray imaging or may perform the blind spot display after the X-ray imaging.

It is possible to display, when the X-ray imaging system 1B performs the above-described blind spot display, an area invisible from the operator D in the real space, using the parallax images generated in the virtual space and the parallax images generated by the optical imaging. The parallax images displayed on the parallax images by the optical imaging are acquired by projecting the blind area, specified in the virtual space, onto the surfaces of the non-transmissive type displays DRB and DLB in the real space.

According to the X-ray imaging system 1B, it is possible to display, even if the position of the blind spot varies according to the movement of the operator D, (A) the movable device existing in the blind spot caused by the fixed device, (B) the fixed device existing in the blind spot caused by the movable device, and (C) the first movable device existing in the blind spot caused by the second movable device. This is because it is unnecessary to optically image the blind spot that occurs when viewed from the operator D. That is, according to the X-ray imaging system 1A, it is possible to improve, when there is the observation target device including at least one movable device movable independently, operability of the movable device by the operator D.

3. Third Embodiment of Image Displaying System 1

Another embodiment of the image displaying system 1 according to the present invention is an industrial robot arm system equipped with an industrial robot that moves the movable device (robot arm) according to an operator's operation. The industrial robot is, for example, a robot that moves robot arms at a manufacturing factory of an automobile to perform spot welding, body painting, and component mounting.

Further, as another embodiment of the image displaying system 1 according to the present invention is a robot arm system for space that moves the movable device (robot arm) according to an operator's operation.

FIG. 12 is a schematic diagram showing the overall configuration of a robot arm system according to a third embodiment.

FIG. 12 shows a robot arm system according to a third embodiment, for example, a space robot arm system 1C. The space robot arm system 1C includes a left robot arm 101 and a right robot arm 102. Each of the robot arms 101 and 102 has joints and has arm portions connected by each joint. The robot arms 101 and 102 are able to move in the same way as human arms. The base arms of the robot arms 101 and 102 are used when exchanging large equipments such as outboard experiment equipments. The tip arms of the robot arms 101 and 102 are used when carrying out detailed work.

Even in the space robot arm system 1C, a part of the right robot arm 102 may enter the blind spot caused by the left robot arm 101 as viewed from the operator of the robot arms 101 and 102.

Therefore, each arm portion of the robot arms 101 and 102 is set as the movable device, and a three-dimensional model of the movable device is stored in advance. Then, the operator wears the wearable device 8A (shown in FIGS. 3A to 3C). The computer generates parallax images including the blind area from the three-dimensional model of the movable device, the arrangement data of the movable device, and the position data and the attitude data of the wearable device 8A. The transmissive type display device 82A of the wearable device 8A displays the parallax images including the blind area. As a result of such display, as explained with FIG. 6C, an image appears in the field of view of the operator wearing the wearable device 8A, the image showing the portion of the right robot arm 102 in the blind spot caused by the left robot arm 101. Therefore, the burden on the operator when operating the robot arms 101 and 102 is reduced.

It goes without saying that the operator may wear the wearable device 8B (FIGS. 7A to 7C) instead of the wearable device 8A. In this case, the computer generates the parallax images including the blind area based on the three-dimensional model of the movable device, the arrangement data of the movable device, and the position and attitude data of the wearable device 8B. The non-transmissive type display device 82B of the wearable device 8B generates and displays the superimposed parallax images. As a result of such display, as explained with FIG. 11, an image appears in the field of view of the operator wearing the wearable device 8B, the image showing the portion of the right robot arm 102 in the blind spot caused by the left robot arm 101. Therefore, the burden on the operator when operating the robot arms 101 and 102 is reduced.

According to the robot arm system 1C, it is possible to display, even if the position of the blind spot varies according to the movement of the operator, (A) the movable device existing in the blind spot caused by the fixed device, (B) the fixed device existing in the blind spot caused by the movable device, and (C) the first movable device existing in the blind spot caused by the second movable device. This is because it is unnecessary to optically image the blind spot that occurs when viewed from the operator. That is, according to the robot arm system 1C, it is possible to improve, when there is the observation target device including at least one movable device movable independently, operability of the movable device by the operator.

4. Fourth Embodiment of Image Displaying System 1

The first embodiment of the image displaying system 1 according to the present invention is the case where the image of the three-dimensional model included in the blind area when viewed from the operator is generated as the parallax images, and where the parallax images are displayed on the displays DLA and DRA of the display device 82A (shown in FIGS. 2A to 2C). In addition, the second embodiment of the image displaying system 1 according to the present invention is the case where the image of the three-dimensional model included in the blind area when viewed from the operator is generated as the parallax images, and where the parallax images are displayed on the displays DLB and DRB of the display device 82B (shown in FIGS. 8A to 8C). However, the image displaying system 1 is not limited to the case where the image of the three-dimensional model is generated as the parallax images, or the case where the image are displayed on the wearable display devices 82A and 82B. For example, the image displaying system 1 may display the parallax images of the three-dimensional model on the operating room display device 53 having a 3D display having a structure capable of displaying parallax images for stereoscopic viewing, or may display a non-parallax image relating to the three-dimensional model on the operating room display device 53 having a 2D display.

Here, when the operating room display device 53 includes the 3D display, the display of the operating room display device 53 may adopt the eyeglass type 3D display described above or the glassless type 3D display.

A case where an image without parallax related to the three-dimensional model is displayed on the display of the operating room display device 53 by using an X-ray imaging system 1D according to the fourth embodiment of the image displaying system 1 will be described. In the overall configuration of the X-ray imaging system 1D, the wearable device 8A, included in the entire configuration of the X-ray imaging system 1A according to the first embodiment shown in FIG. 1 is merely replaced with a wearable device 8D, the explanation of the configuration is omitted.

FIG. 13 is a block diagram showing functions of the X-ray imaging system 1D.

As the processing circuitry 91 executes the program, the X-ray imaging system 1D achieves a movable device data acquiring function 91a, a three-dimensional model acquiring function 91b, a three-dimensional model arranging function 91c, a wearable device data acquiring function 91d, an image generating function 91e, and an X-ray imaging function 91f. It is to be noted that the functions 91a to 91f are achieved by executing the program, but it is not limited to that case. All or a part of the functions 91a to 91f may be achieved as a circuit such as the ASIC in the X-ray imaging system 1D.

In FIG. 13, same reference numerals are given to same members as those shown in FIGS. 3 and 8, and the explanation will be omitted.

The image generating function 91e sets the observation area IA in the virtual space as described with reference to FIGS. 5A to 5C (or FIGS. 10A to 10C), generates an image acquired by superimposing the image, related to the blind area with the observation position PA' as the viewpoint, on the image related to the observation area IA, and displays the superimposed image on the operating room display device 53. Here, the image generating function 91e may update the superimposed image displayed on the operating room display device 53 at fixed or irregular time intervals, or may update, by the operation of the operator D, the superimposed image displayed on the operating room display device 53. This is to prevent the angle of the display image from being instantaneously changed following the movement of the operator D.

According to the X-ray imaging system 1, effects equivalent to those of the X-ray imaging systems 1A and 1B described above can be obtained. Further, according to the X-ray imaging system 1D, there is also an effect that the operator D does not need to wear the display devices 82A and 82B.

According to at least one embodiment described above, it is possible to improve operability of the movable device by the operator D.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An image displaying system comprising:
an observation target device existing outside a human body in a three-dimensional real space;
a display configured to display an image; and
processing circuitry configured to
acquire a three-dimensional virtual model in which an external shape of the observation target device is simulated and arrange the three-dimensional virtual model in a three-dimensional virtual space,
acquire data indicating a relative positional relationship between an operator and the observation target device,
generate, when the observation target device is partially hidden in a blind area, parallax images of a three-dimensional virtual model part included in the blind area when viewed from the operator, based on the data indicating the relative positional relationship and on the three-dimensional virtual model arranged in the three-dimensional virtual space, the three-dimensional virtual model part being a part of the three-dimensional virtual model, and display the parallax images on the display, wherein the blind area is that a direct field of view by the operator may be blocked and existing between the operator and the observation target device and outside the human body in the three-dimensional real space, and the observation target device may be partially hidden in the blind area depending on a non-cycled movement of the observation target device or the operator.

2. The image displaying system according to claim 1, further comprising a wearable device being wearable by the operator, the wearable device including the display being capable of displaying the parallax images.

3. The image displaying system according to claim 2, wherein
the display includes two displays capable of displaying the parallax images, the two displays displaying the parallax images, respectively.

4. The image displaying system according to claim 3, wherein
the processing circuitry is configured to generate, based on data on a position and an attitude of the wearable device and the three-dimensional virtual model arranged in the three-dimensional virtual space, the parallax images of the three-dimensional virtual model part included in the blind area.

5. The image displaying system according to claim 3, wherein
the processing circuitry is configured to
set an observation area having a position of the wearable device as a base point in the three-dimensional virtual space, and
specify, as the blind area, an area indicating a three-dimensional virtual model element different from a three-dimensional virtual model element closest to the set position, the indicating area being included in the observation area, and the three-dimensional virtual model elements each being of a plurality of the three-dimensional virtual model.

6. The image displaying system according to claim 3, wherein
the wearable device includes two optical imaging devices for acquiring parallax images by optical imaging,
each of the two displays is non-transmissive type, and
the wearable device is configured to superimpose the parallax images including the blind area on the parallax images acquired by the optical imaging, thereby generating and displaying the superimposed parallax images on the two displays.

7. The image displaying system according to claim 6, wherein
the two displays are capable of adjusting the transparency of the parallax images including the blind area.

8. An X-ray imaging system comprising:
an observation target device including an arm device, the observation target device existing outside a human body in a three-dimensional real space;
a display configured to display an image; and
processing circuitry configured to
acquire a three-dimensional virtual model in which an external shape of the observation target device is simulated and arrange the three-dimensional virtual model in a three-dimensional virtual space,
acquire data indicating a relative positional relationship between an operator and the observation target device,
generate, when the observation target device is partially hidden in a blind area, parallax images of a three-dimensional virtual model part included in the blind area when viewed from the operator, based on the data indicating the relative positional relationship and on the three-dimensional virtual model arranged in the three-dimensional virtual space, the three-dimensional virtual model part being a part of the three-dimensional virtual model,
display the parallax images on the display device, and
perform an X-ray imaging on a subject, wherein
the blind area is that a direct field of view by the operator may be blocked and existing between the operator and the observation target device and outside the human body in the three-dimensional real space, and
the observation target device may be partially hidden in the blind area depending on a non-cycled movement of the observation target device or the operator.

9. The X-ray imaging system according to claim 8, further comprising a wearable device being wearable by the operator, the wearable device including the display being capable of displaying the parallax images.

10. The X-ray imaging system according to claim 9, wherein
the display includes two displays capable of displaying the parallax images, the two displays displaying the parallax images, respectively.

11. The X-ray imaging system according to claim 10, wherein
the processing circuitry is configured to
set an observation area having a position of the wearable device as a base point in the three-dimensional virtual space, and
specify, as the blind area, an area indicating a three-dimensional virtual model element different from a three-dimensional virtual model element closest to the position, the indicating area being included in the observation area, and the three-dimensional virtual model elements each being of a plurality of the three-dimensional virtual model.

12. The X-ray imaging system according to claim 10, wherein
the wearable device includes two optical imaging devices for acquiring the parallax images by optical imaging,
each of the two displays is non-transmissive type, and
the wearable device is configured to superimpose the parallax images including the blind area on the parallax images acquired by the optical imaging, thereby generating and displaying the superimposed parallax images on the two displays.

13. The X-ray imaging system according to claim 12, wherein
the two displays are capable of adjusting the transparency of the parallax images including the blind area.

14. The X-ray imaging system according to claim 10, wherein
the arm device includes a C-arm or an Ω-arm supporting an X-ray emitting device and an X-ray detecting device, the arm being capable of rotating or arc moving.

15. The X-ray imaging system according to claim 10, wherein
the arm device includes two arms each supporting a set of an X-ray emitting device and an X-ray detecting device, the two arms being independently movable.

16. The X-ray imaging system according to claim 10, wherein
   the observation target device further includes a table capable of sliding, tilting or rolling.

17. The X-ray imaging system according to claim 10, wherein
   the observation target device further includes a display device capable of sliding or rotating.

18. The X-ray imaging system according to claim 10, wherein
   the observation target device includes at least one movable device, and a gantry device of an X-ray CT (Computed Tomography) device which is a fixing device.

* * * * *